United States Patent [19]

Kern

[11] Patent Number: 5,409,827
[45] Date of Patent: Apr. 25, 1995

[54] BLENDED BOVINE SERA CELLULAR GROWTH MEDIA AND THEIR METHODS OF PRODUCTION AND USE

[75] Inventor: Dale G. Kern, Logan, Utah

[73] Assignee: HyClone Laboratories, Inc., Logan, Utah

[21] Appl. No.: 148,064

[22] Filed: Nov. 4, 1993

Related U.S. Application Data

[63] Continuation of Ser. No. 32,412, Mar. 15, 1993, abandoned, which is a continuation of Ser. No. 663,377, Feb. 28, 1991, abandoned.

[51] Int. Cl.$^6$ .................... C12N 5/00; A61K 35/14; A61K 35/16
[52] U.S. Cl. .................... 435/240.3; 435/240.2; 435/240.21; 435/240.26; 424/529; 424/531
[58] Field of Search ............ 435/240.3, 240.31, 240.2, 435/240.23, 240.26, 240.1; 424/529, 531

[56] References Cited

U.S. PATENT DOCUMENTS

| | | | |
|---|---|---|---|
| 3,429,867 | 2/1969 | Bozicevich | 260/112 |
| 4,007,008 | 2/1977 | Becker et al. | 23/230 B |
| 4,081,431 | 3/1978 | Stephan et al. | 260/112 |
| 4,136,094 | 1/1979 | Condie | 260/122 |
| 4,473,647 | 9/1984 | Carpenter et al. | 435/240 |
| 4,533,634 | 8/1985 | Maldonado et al. | 435/240 |

OTHER PUBLICATIONS

Torres et al, FASEB, 2(6), 1988, Abstract #7977.
Chang, R. Shihman et al. "Macromolecular Growth Requirements of Human Cells in Continuous Culture," *P.S.E.B.M.* vol. 102, pp. 213–217 (1959).
Fisher et al., "Molecular Growth Requirements of Single Mammalian Cells: The Action of Fetuin in Promoting Cell Attachment to Glass," *Biochemistry*, vol. 44, pp. 4–10 (1958).
Fisher, Harold W. et al., "Molecular Growth Requirements of Single Mammalian Cells, III. Quantitative Colonial Growth of Single S3 Cells in a Medium Containing Synthetic Small Molecular Constituents and Two Purified Protein Fractions," *J. Exp. Med.*, vol. 109, pp. 649–659.
Ham, Richard G. et al., "Media and Growth Requirements," *Methods in Enzymology*, vol. LVIII, pp. 44–93 (1979).

(List continued on next page.)

Primary Examiner—Douglas W. Robinson
Assistant Examiner—Susan M. Dadio
Attorney, Agent, or Firm—Workman, Nydegger & Seeley

[57] ABSTRACT

The present invention provides media and methods for the maintenance or promotion of growth of a cellular line, particularly a hybridoma cellular line. A serum blend is disclosed comprising fetal bovine serum and agamma bovine calf serum. The serum blend is added to other types of support media and can be placed in association with a hybridoma cellular line. The cellular media are preferably employed with hybridoma cellular lines in an environment having a carbon dioxide atmosphere in the range from about ambient levels to 10%, and at a temperature in the range from about 32° C. to 40° C.

In addition, the present invention provides for cellular lines maintained and grown in association with such a serum blend. Also, a serum used in a medium for producing diagnostic and therapeutic biologicals from cellular lines, particularly, hybridoma cellular lines, comprising a serum blend of fetal bovine serum and agamma bovine calf serum is provided. Finally, the present invention discloses a composition produced by an organism grown in a medium for promoting the growth of organisms, particularly hybridoma cellular lines, the composition being an organic product secreted by an organism maintained in a media containing a serum blend of fetal bovine serum and agamma bovine calf serum.

64 Claims, 15 Drawing Sheets

OTHER PUBLICATIONS

Holmes, Richard et al., "Serum Fractionation and the Effects of Bovine Serium Fractions on Human Cells Grown in a Chemically Defined Medium," *The Journal of Biophysical and Biochemical Cytology*, vol. 10, pp. 389–401 (1961).

Jacquez, John A. et al., "Tissue Culture Media: The Essential Non-Dialyzable Factors in Human Placental Cord Serum," pp. 765–773, Division of Experimental Chemotherapy, The Sloan-Kettering Institute for Cancer Research, New York (1951).

Jakoby, William B., "Cell Culture," *Methods in Enzymology: vol. LVIII*, pp. 77–93, Academic Press (1979).

Kent, H. Naim et al. "Changes in Serum Proteins During Growth of Malignant Cells in Vitro," *P.S.E.B.M.*, vol. 94, pp. 205–208 (1957).

Lieberman, Irving et al., "A Protein Growth Factor for Mammalian Cells in Culture," *J. Biol. Chem.*, vol. 223, pp. 637–642.

Parker, Raymond C., "Stationary Fluid Culture" *Methods of Tissue Culture*, p. 193 (1965).

Puck, Theodore T. et al., "Mammalian Cell Growth Proteins, I. Growth Stimulation by Fetuin," *Biochemistry*, vol. 59, pp. 192–199 (1967).

Robbins, Stanley L., Chapter 10: "Minerals and Pigments" from *vol. I: Pathology*, p. 404.

Rothblat, George H. et al., Chapter 3: "The Role of Serum in the Control of Multiplication of Avian and Mammalian Cells in Culture," *Growth, Nutrition, and Metabolism of Cells in Culture*, pp. 49–81 (1972).

Rothblat, George H. et al., Chapter 9: "Cellular Sterol Metabolism" from "vol. 1: Growth, Nutrition, and Metabolism of Cells in Culture," pp. 302–306 (1972).

Toddaro et al., "Serum Albumin Supplemented Medium for Long-Term Cultivation of Mammalian Fibroblast Strains," *P.S.E.B.M.*, vol. 116, pp. 688–692 (1964).

"Replacement of Serum by Hormones Permits Growth of Cells in a Defined Medium," *Nature*, vol. 259, pp. 32–34 (1976).

Product brochure from Biocell Laboratories (undated).

BLENDED BOVINE SERA CELLULAR GROWTH MEDIA AND THEIR METHODS OF PRODUCTION AND USE

This application is a file wrapper continuation application of U.S. application Ser. No. 08/032,412, filed Mar. 15, 1993, now abandoned, which was a file wrapper continuation application of U.S. application Ser. No. 07/663,377, filed Feb. 28, 1991, now abandoned, for BLENDED BOVINE SERA CELLULAR GROWTH MEDIA AND THEIR METHODS OF PRODUCTION AND USE.

BACKGROUND

1. The Field of the Invention

This invention relates to cellular support media and to methods by which to prepare cellular support media for maintaining and supporting either a primary or established cellular line. More particularly, the present invention relates to media and methods that contain bovine calf serum to support either primary or established cellular lines, particularly hybridoma cellular lines, or for use in the production of diagnostic or therapeutic biologicals.

2. The Background Art

It is well-known that animal and plant cells may be grown in vitro in liquid culture media, i.e., tissue culture media. Such media usually contain a wide array of different components, including various nutrients and salts that promote the maximum growth of the cultured cells. Among the most important of these different components are the growth support factors found in the culture medium.

Growth support factors are specific organic compounds that are required in very small amounts and often cannot be synthesized by the cell. Substances frequently serving as growth support factors are vitamins, amino acids, purines, and pyrimidines and peptides, steroids, and proteins. Some organisms are able to synthesize all of these compounds, whereas others require the addition of one or more to the culture medium.

Cells grown in vitro by tissue culture methods are used for many different purposes; for example, for the production of enzymes, secondary byproducts; or for the general testing of drugs, carcinogenic agents, and the like. In vitro growth of animal cells lines has recently acquired new relevance with the development of cell fusion, and the preparation of hybridomas and their associated products, e.g., monoclonal antibodies.

Cells can be obtained from lines that can be characterized as either primary or established. The formation of a cell line from a primary culture implies: (1) an increase in total cell number over several generations, (2) that cells or cell lineages with similar high growth capacity will predominate, and (3) a degree of uniformity in the cell population will result. The line may be characterized, and those characteristics will apply for most of its finite life span. The derivation of "established" (or "continuous") cell lines usually implies a phenotypic change or transformation.

Hybridoma cell lines are artificially created to be employed in immunological studies and the production of diagnostic or therapeutic biologicals production., A typical immune response results in the production of a broad spectrum of antibodies of varying affinities for any given antigen. The antibodies directed toward a particular determinant will represent but a small proportion of the total antibody pool. If one could isolate a hybrid clone of B cells that are responsible for making a particular antibody of interest, a source of monospecific or monoclonal antibody would be available.

Techniques are now available for isolating and growing single hybrid B-lymphocytes for indefinite periods of time. This procedure, called the "hybridoma technique," combines the unlimited division properties of a cancer cell with the monoclonal antibody production of a single B-lymphocyte. In practice, myeloma cells are fused with a pool of B cells removed from a mouse previously immunized with the antigen of interest; agents (such as polyethylene glycol) are added to the mixture to promote fusion.

Since myeloma cells are themselves B-lymphocytes, a variant myeloma cell line that has lost the ability to make immunoglobulin is routinely employed in hybridoma production. After fusing, the heterokaryotic hybrid cell undergoes a nuclear fusion and eventually results in antibody producing cells that can be selectively cloned and subsequently injected into an animal, where it grows as a myeloma tumor secreting monoclonal antibodies. The immunoglobulin molecules produced by a hybridoma are characteristic of the normal B cell to which the malignant cell was fused. The resulting hybridoma population is screened using various immunological and biochemical techniques to identify the clone producing the monoclonal antibody of interest.

The art has long established that one of the essential components for tissue culture media is animal serum, i.e,, fluid taken from clotted blood (as opposed to plasma which is obtained via centrifugation of blood prior to clotting). Most preferably, fetal bovine serum is employed for tissue culture media. This type of serum lacks high concentrations of the components that inhibit cell growth, and contains undefined factors that support cell growth in vitro.

Fetal bovine sera, as opposed to other types of sera, are employed in culture media because organisms, from which sera are obtained, at an early age have less experienced immune responses. This is possible since fetal bovine sera comes from animals taken from the in utero state where their systems have not come into contact with high levels of contaminants. Fetal bovine serum contains factors that promote development of the fetus and are thereby often necessary for a cell's maintenance and support in vitro.

The use of fetal bovine serum, however, is troubled by a lack of sufficient supply. Because fetal bovine serum can only be derived from pregnant cows, the sources from which the serum can be obtained are limited. Moreover, the number of available cows can vary depending upon activity in the meat industry and the open markets wherein the demand for beef can fluctuate without warning.

The production of an alternative fetal bovine serum to meet the problems with supply is possible. Production, however, would require that the alternative serum be made from the constituent substances which comprise fetal bovine serum. This procedure is obviously expensive and time consuming. Therefore, the increasing demand for the limited supplies of fetal bovine serum forces researchers to look for other alternatives for fetal bovine serum available in great quantities.

The use of fetal bovine serum is also troubled by the poor characterization of its ingredients. Typically, the cellular lines grown in the fetal bovine serum are employed for testing and it may be necessary to identify the factors that support the cellular growth. Identification of the factors can take a long period of time and quite a bit of effort to perform several assays on the fetal bovine serum. This is important to scientists conducting tests with media employing the sera; use of sera whose ingredients are better characterized will promote research and valuable testing.

In addition, the use of fetal bovine serum is troubled due to the undefined amount of time the serum remains stable while stored. Fetal bovine serum is comprised of various ingredients (such as vitamins and proteins) that can become inactivated over time. Therefore, a large amount of the serum can not be kept over extended periods of time and, therefore, the serum must constantly be reordered, which as previously mentioned, may not be possible since the serum supply is often limited.

Furthermore, the use of fetal bovine serum is troubled by the costs for this type of serum which can preclude the existence of cell culture technology because of the expenses involved in the acquisition of fetal bovine serum. An alternative serum available at a fraction of the cost of fetal bovine serum would be in great demand. This factor increases the emphasis society has placed on researchers to find a cost-effective alternative for fetal bovine serum.

This is particularly important to the development of hybridoma cellular lines. Hybridoma cellular lines are artificially created to be employed in immunological studies and the production of diagnostic or therapeutic biologicals. High costs for fetal serum (due to shortages in supply, short time the serum remains stable, and the like) may preclude the existence of hybridoma technology due to economic considerations associated with fetal bovine serum with respect to hybridoma cellular lines.

A need, therefore, exists for media used to maintain or promote primary or established cellular lines that can meet the existing and anticipated increasing future demand for growth media. The media should be available at a low price so that the economically feasible growth of cellular lines that utilize the media is promoted. This is particularly true of hybridoma cellular lines that are increasingly being employed to produce diagnostic and therapeutic biologicals. Likewise, a need exists to decrease the cost of fetal bovine serum-containing media in order to enable the economically feasible growth of hybridoma cells.

Moreover, the cost of reagents employed to make up media used to maintain and promote cellular lines needs to be lower. If reagents can be purchased at a lower price, the cost of the media comprising the reagents can likewise be purchased at a lower price.

Similarly, a need exists to provide a serum-containing media that will remain in a stable condition over an extended period of time and will not require replacement if stored for extended periods of time. Frequent replacement of sera subject to rapid degradation necessarily results in higher costs to the individual employing the sera.

A need further exists to provide serum-containing media that does not suffer from poor characterization of its ingredients. Scientists can proceed with various tests knowing the precise components comprising their testing media.

BRIEF SUMMARY AND OBJECTS OF THE INVENTION

It is, therefore, one object of the present invention to provide media for the maintenance or promotion of a primary or established cellular line that does not employ a substance that is difficult to manufacture.

It is another object of the present invention to lower the cost of media used to maintain or promote primary or established cellular lines so that the economically feasible growth of the cellular lines that employ the media is promoted. This is particularly true of hybridoma cellular lines that are increasingly being employed to produce diagnostic or therapeutic biologicals.

It is a related object of the present invention to decrease the cost of the reagents employed to make up media used to maintain and promote cellular lines. If reagents can be purchased at a lower price, the cost of the media comprising the reagents can likewise be purchased at a lower price.

Another object of the present invention is to decrease the cost of fetal bovine serum-containing media in order to enable the economically feasible growth of cultures containing such serum.

A further object of the present invention is to provide serum-containing media that does not suffer from poor characterization of its ingredients.

Still another object of the present invention is to provide serum-containing media that will remain in a stable condition over an extended period of time and will not require replacement if left on a laboratory shelf for ally period of time.

Additional objects and advantages of the invention will be set forth in the description that follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, media and methods are provided for maintaining and promoting a cellular line, particularly a hybridoma cellular line. In the present invention, a serum is disclosed comprising a serum blend of fetal bovine serum in a concentration in the range from about one (1%) to about forty percent (40%) and agamma bovine calf serum in a concentration in the range from about sixty percent (60%) to about ninety-nine percent (99%), together with the other appropriate and typical components for promoting the growth of hybridomas. As discussed in greater detail hereafter, agamma bovine calf serum is bovine calf serum produced by methods known in the art utilizing the blood of veal calves in which immunoglobulins have been substantially removed from the serum.

While the present invention could comprise sera blended in the range described above, for some embodiments it is possible that a serum blend of fetal bovine serum in a concentration range in the range from about four percent (4%) to about twenty percent (20%) and agamma bovine calf serum in a concentration in the range from about eighty percent (80%) to about ninety-six percent (96%) could be employed. Also, in the most preferred embodiment of the present invention sera would be blended with fetal bovine serum in a concentration in the range from about six percent (6%) to about fifteen percent (15%) and agamma bovine calf serum in a concentration in the range from about eighty-five percent (85%) about ninety-four percent (94%).

The present invention also contemplates a method for preparing a serum to be added to a medium for maintaining and promoting the growth of a cellular line, particularly a hybridoma cellular line. The method comprises the steps of preparing an agamma bovine calf serum and then adding fetal bovine serum to the resulting solution. The addition of the fetal bovine serum to the resulting solution to comprise the serum blend of the present invention is accomplished according to the concentration ranges covered by any of the embodiments disclosed by the present invention.

Other methods are also disclosed by the present invention. A method for preparing a medium for maintaining or promoting the growth of a cellular line is disclosed. Particularly a method for preparing a medium for maintaining or promoting the growth of a hybridoma cellular line, that must be grown in some type of medium.

Once a blend comprised of agamma bovine calf serum and fetal bovine serum is provided, as indicated in the previous discussion, the method comprises the further step of adding to the blend a basal culture medium. In some of the embodiments of the present invention one of the following basal culture media are employed: Ham's F12 TM or Minimum Essential Medium Eagle TM or Dulbecco's Modified Eagle's Medium TM. Of course as discussed hereafter, other basal culture media may be used.

Also, a method for maintaining and promoting the growth of a cellular line is disclosed. The method is comprised of steps for obtaining a cellular line and placing the cellular line in the presence of fetal bovine serum-containing medium that maintains and promotes the growth of the cellular line. In particular, the method maintains and promotes the growth of hybridoma cellular lines.

Finally, the present invention provides for a serum for use in a medium for producing diagnostic and therapeutic biologicals from cellular lines, in particular hybridoma cellular lines. The serum comprises a blend of fetal bovine serum and agamma bovine calf serum. The present invention would also cover the diagnostic and therapeutic biologicals obtained from the cellular lines maintained in the serum.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

A. Blended Sera

Figure 1:
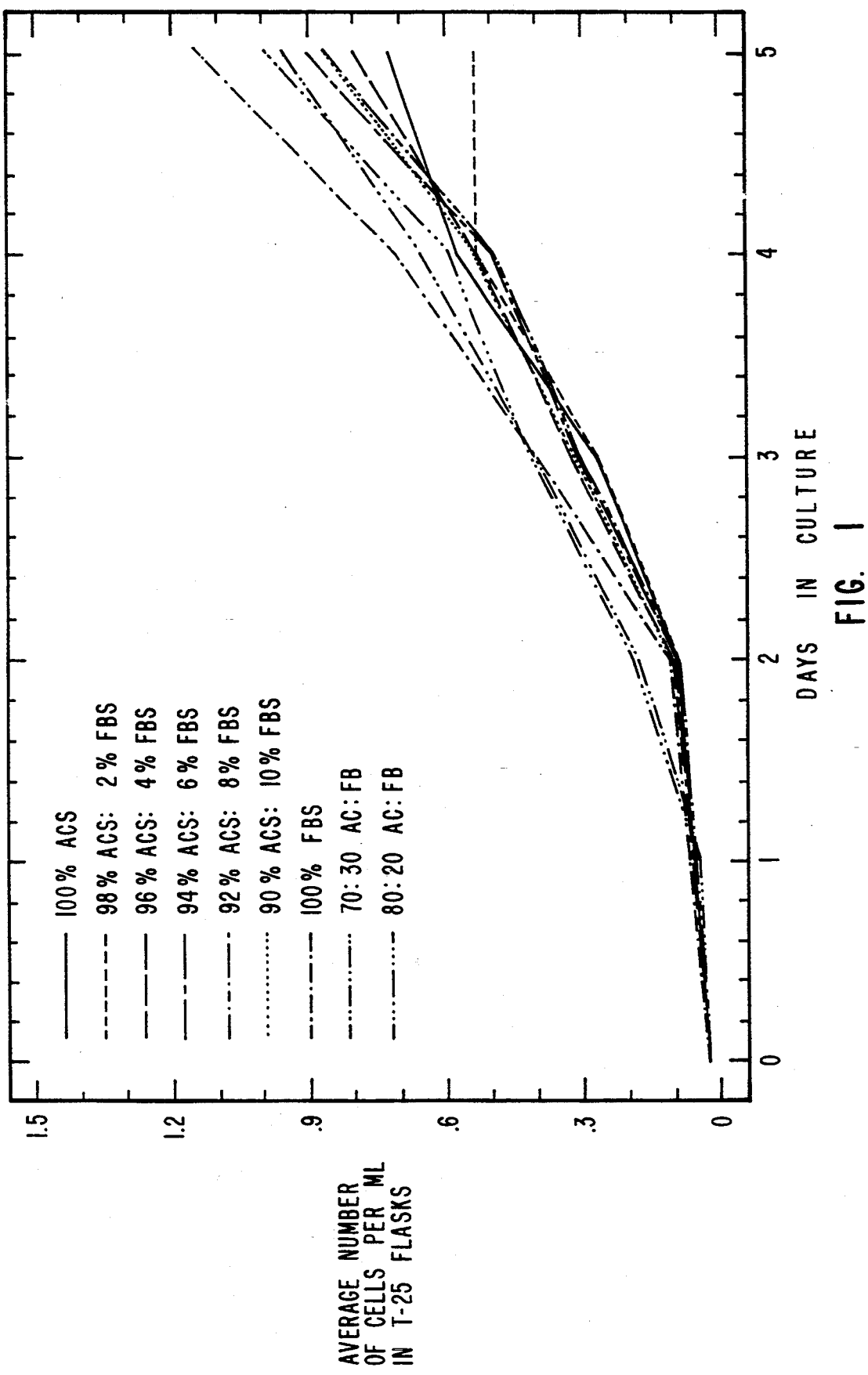
FIG. 1 shows a chart which compares the growth over time of the Sp2/0 cellular line in a medium containing various inventive serum blends. The medium has 5% serum in DME medium.

The present invention is directed to novel blended sera and serum-containing media that are particularly useful to propagate certain cell lines, particularly hybridoma cell lines. More specifically, the present invention provides blended sera containing fetal bovine serum as a minor component in agamma bovine calf serum-containing media that are particularly useful in promoting the growth of hybridoma cell lines. The use of the agamma bovine calf serum-containing media have proven to be satisfactorily equivalent to the use of media employing only fetal bovine sera.

Agamma bovine calf sera have been defined by industry standards to mean bovine calf sera that have been treated to remove substantially all of the antibodies from the sera. The pertinent antibodies to be removed include any of the body immunoglobulins that are produced in response to specific antigens and that counteract their effects, especially by neutralizing toxins, agglutinating bacteria or cells, and precipitating soluble antigens. The removal of antibodies from the sera prevents the antibodies from entering into side reactions when the sera are employed in research studies.

The present invention preferably employs agamma bovine calf sera that is different from other agamma bovine calf sera produced by current industry standards. One of the more notable differences is that agamma bovine calf sera of the present invention are characterized by a lipid concentration that is higher than the lipid concentration found in other agamma bovine calf sera. The agamma bovine calf serum of the present invention have a lipid concentration in the range from about ten (10) mg/dl, milligrams per deciliter, to about one hundred twenty (120) mg/dl prior to blending with the fetal bovine serum.

Another difference between agamma bovine calf sera of the present invention and other agamma bovine calf sera produced by current industry standards is that agamma bovine calf sera of the present invention are characterized by a higher level of transferrin than are other agamma bovine calf sera. The agamma bovine calf sera of the present invention have a transferrin level in the range from about four hundred (400) mg/dl to about eight hundred (800) mg/dl prior to blending with the fetal bovine serum.

The present invention covers sera that comprise a serum blend of fetal bovine serum in a concentration in the range from about one percent (1%) to about forty percent (40%) and agamma bovine calf serum in a concentration in the range from about sixty percent (60%) to about ninety-nine percent (99%), together with the other appropriate and typical components for promoting the growth of cellular lines, particularly hybridoma cellular lines.

The amount of fetal bovine serum that is blended with agamma bovine calf serum can be a factor that is dependent upon cost and supply. Sera employing only about one percent (1%) fetal bovine sera and about ninety-nine percent (99%) agamma bovine calf sera are less expensive and in greater supply than sera employing about forty percent (40%) fetal bovine sera and about sixty percent (60%) agamma bovine calf sera. This is because agamma bovine calf sera are less expensive and in greater supply than fetal bovine sera.

Because of the unexpected results of the present invention, however, the ability of the sera blended at various ranges to maintain and promote growth of cellular lines is not a factor to be considered in the amount of fetal bovine sera to be blended with agamma bovine calf sera. Sera blended with fetal bovine sera and agamma bovine calf sera at the ranges described above maintain and promote the growth of cellular lines about as well as sera comprised only of fetal bovine sera. In some instances the blended sera was superior to fetal bovine sera for maintaining and promoting the growth of cellular lines.

While the present invention could comprise sera blended in the range described above, for some embodiments it is possible that a serum blend of fetal bovine serum in a concentration in the range from about four percent (4%) to about twenty percent (20%) and agamma bovine calf serum in a concentration in the range from about eighty percent (80%) to about ninety-six percent (96%) could be employed. Also, in the most preferred embodiment of the present invention sera would be blended with fetal bovine serum in a concentration in the range from about six percent (6%) to about fifteen percent (15%) and agamma bovine calf serum in a concentration in the range from about eighty-five percent (85%) to about ninety-four percent (94%).

The use of sera that does not employ large amounts of fetal bovine sera can be realized as advantageous in light of the expense of fetal bovine serum. The use of the sera can also be realized as advantageous considering that the sera and media of the present invention are yet effective at maintaining and supporting a cellular line, even without employing large amounts of fetal bovine serum. The sera and media of the present invention maintain and promote the growth of a cellular line about as well as, and in some instances better than fetal bovine sera and fetal bovine sera-containing media.

Relatedly, because of the lower costs of sera and media which do not employ large amounts of fetal bovine sera, the economically feasible growth of cellular lines that employ the sera and media are promoted. This is particularly true of hybridoma cellular lines that are increasingly being employed to produce diagnostic or therapeutic biologicals. Diagnostic or therapeutic biologicals are biologically derived compositions which are employed in diagnostic or therapeutic processes.

Several companies currently supply the agamma bovine calf sera that comprises the present invention. A list of some of some of these companies has been included in Table I. It has been found that agamma bovine calf serum, currently marketed by HyClone Laboratories, Inc. and sold under the trade name, AlphaCalf Serum TM (catalog #A-2161-L) is most preferred.

AlphaCalf serum is a type of agamma bovine calf serum. The serum derived from veal calves contains more transferrin (i.e., an iron-binding protein that transports iron into cells) than serum produced from non-veal calves. This is because when bovine calf sera are processed to remove immunoglobulins to produce agamma bovine calf sera, a portion of the transferrin, and therefore iron, contained in the bovine calf sera are lost. High concentrations of transferrin are important to agamma bovine calf sera because of the nutritional importance a high supply of iron attached to the transferrin represents.

The veal calves used to supply the bovine calf sera are raised on low-iron diets in order to produce high concentrations of transferrin. Next, the bovine calf serum is strained in order to defibrinize the organically obtained solution. The presence of clotting factors can complicate experimental results obtained from the use of the bovine calf serum. The defibrination step is accomplished by straining the bovine calf serum through a fine plastic mesh.

Then, immunoglobulins and proteins similar in nature to immunoglobulins are removed from the bovine calf sera. As mentioned previously, some transferrin is removed as well and thus the value in starting with a material that is higher than normal in transferrin. The residual compound in the serum is removed by dialysis and osmotic strength of the solution is restored to physiological levels. The final preferred material, agamma bovine calf serum, contains very low levels of immunoglobulin (concentration similar to fetal bovine serum) and very low levels of dialyzable small molecules (e.g., sugar, vitamins, amino acids, nucleotides, metals, and the like).

In the preferred embodiment of the present invention, it was found that it is best to employ agamma bovine calf serum that has a significant lipid concentration. The types of lipids need not be carefully controlled. Although, where different types of lipids have been employed in the agamma bovine calf serum, characterized by high and low densities, various concentrations of the lipids are preferred.

The use of the following lipids is presented as an example of the various concentrations and different types of lipids that may be employed in the present invention. The examples, however, are given by way of illustration only, and the present invention is not meant to be limited to the foregoing. Agamma bovine calf serum may be comprised of cholesterol. The concentration of the cholesterol in the agamma bovine calf serum is in the range from about forty (40) to one hundred twenty (120) mg/dl.

Agamma bovine calf serum may also be comprised of triglycerides. The concentration of the triglycerides in the agamma bovine calf serum is in the range from about four (4) to ten (10) mg/dl.

It has also been discovered that in the preferred embodiment of the present invention, it is easier in the manufacturing process to employ agamma bovine calf serum that is not supplemented with iron. The use of iron supplemented bovine calf serum often complicates the preparation of the blended sera at a specified iron concentration. Instead, it has been found that it is easier to supplement the prepared blended sera with iron to arrive at a desired concentration.

The process of the present invention would involve first mixing agamma bovine calf serum with fetal bovine serum. This step is followed by measurement of the iron binding capacity of the mixture. Thereafter, sufficient amounts of an iron salt-containing solution is added to increase the iron of the blend to a certain level of the total iron binding capacity. Finally, it is necessary to merely measure the percent of bound iron as a final quality control step.

It is also possible to first measure the individual iron binding capacities of agamma bovine calf serum and fetal bovine serum. This process is known to those skilled in the art and involves a determination of the transferrin levels contained in the sera being measured. Next, each would be supplemented separately with an iron salt-containing solution to a certain level of the total iron binding capacity. Finally, the two supplemented sera would be combined and the percent of bound iron would be measured as a final quality control step.

Generally, blended sera can be supplemented with iron in the range from about ten percent (10%) to one hundred percent (100%) of the iron-binding capacity of the sera to be effective. It has been found, however, that blended sera supplemented with iron in the range from about fifty percent (50%) to about one hundred percent (100%) can be even more effective. In the most preferred embodiment, blended sera supplemented with iron in the range from about sixty percent (60%) to about eighty-five percent (85%) is most effective.

In addition the inventive sera can be used for producing diagnostic and therapeutic biologicals from organisms. The sera comprises a serum blend of fetal bovine serum and agamma bovine calf serum in the range of concentrations previously discussed, as well as the alternative inventive modes previously discussed. Biologicals obtained from organisms grown in the inventive sera are distinguishable from biologicals obtained from organisms not grown in the inventive sera. Any such distinctions or remarkable features of the biologicals obtained from organisms grown in the inventive sera can be shown by methods known in the art. The types of biologicals produced by organisms grown in the inventive sera include proteins, carbohydrates, nucleic acids, and other such organic molecules.

B. Method for Preparing the Blended Sera

A method for preparing the blended sera for use in a medium for promoting the growth of hybridoma cellular lines is also disclosed. The method is comprised of the steps of preparing the agamma bovine calf serum as indicated above. Thereafter, fetal bovine serum is added to agamma bovine calf serum in the effective range levels indicated above. In addition, the blended sera may be supplemented with iron at the iron-binding capacity levels indicated above. Finally, the serum can be sterilized by filtration.

Most often, blended serum is not utilized by itself to maintain and promote the growth of a cellular line. Instead, blended serum is added to any one of many kinds of basal culture media. Thus, the present invention also covers fetal bovine serum-containing media that are comprised of the inventive sera disclosed above and a basal culture media.

Use of the basal culture media occurs because the growth factors and various other elements in sera that represent such a nurturing relationship with hybridoma cellular lines can have an inhibitory effect when employed in concentrated solutions. Therefore, the basal culture media dilute the sera to promote their stimulation of cellular growth.

Examples of some, but not all, of the basal culture media which may be employed with the present invention include Ham's F12 ™, Minimum Essential Medium Eagle ™, and Dulbecco's Modified Eagle's Medium ™. A more complete listing of commonly used basal culture media is included as Table II. The basal culture medium provides various elements (such as minerals, salts, simple inorganic salts, trace elements, vitamins, amino acids, nucleotides, sugars, and the like) to cells grown in them.

One important feature of the basal culture medium is its buffer system. The pH of the inventive media is controlled by various acids and bases that make up the buffer system. Cellular lines grown in the inventive media may not require the need for atmospheric controls placed in coordination with the cellular incubations. Nevertheless, such controls are usually employed.

The range of the concentrations of the inventive sera in the fetal bovine serum-containing media is in the range from about one hundredth of one percent (0.01%) to essentially one hundred percent (100%). More effective ranges, nevertheless, are employed in the preferred embodiment of the present invention. Concentrations in the range from about two percent (2%) to about forty percent (40%) are employed.

Preferably, the range of the concentrations of the inventive sera in the fetal bovine serum-containing media is in the range from about five percent (5%) to about twenty percent (20%). This is because this is the range of concentrations that most scientists employ serum in a media. The most preferred concentration of the inventive sera in the fetal bovine serum-containing media, however, would be about ten percent (10%) since this is the concentration that is the standard for most industries employing serum-containing media.

Certain factors affect how much of the inventive sera one would employ in fetal bovine serum-containing media. Examples of such factors include cost, inhibition of cell growth by cells grown in the sera containing media by concentrations of sera that are too high, and the fact that the more sera employed results in higher protein concentrations of the medium and therefore increased difficulty in purifying desired products from the culture medium.

The inventive sera and the fetal bovine serum-containing media can also be a part of other types of preparation or mixtures as well. The combination may be useful as a diluent in place of fetal bovine serum. Some employ fetal bovine serum directly in diagnostic kits to employ the high protein (and perhaps lipid) content to block certain undesirable reactions that would occur in the absence of the fetal bovine serum. Hence, the inventive sera may be employed at about one hundred percent (100%) in some processes.

In addition, the present invention provides for a composition secreted by an organism grown in a medium for promoting the growth of organisms, in particular hybridomas. The composition comprises an organic product made by an organism maintained in a media containing a serum blend of fetal bovine serum in a concentration in the range from about one percent (1%) to about forty percent (40%) and agamma bovine calf serum in a concentration in the range from about sixty percent (60%) to about ninety-nine percent (99%), said serum blend having the appropriate components for promoting the growth of hybridomas. The more preferred media and sera and methods for production of same are also included.

The amount of fetal bovine serum that is blended with agamma bovine calf serum, the blended serum placed in the medium, can be a factor that is dependent upon cost and supply. Sera employing only about one percent (1%) fetal bovine sera and about ninety-nine percent (99%) agamma bovine calf sera are less expensive and in greater supply than sera employing about forty percent (40%) fetal bovine sera and about sixty percent (60%) agamma bovine calf sera. This is because agamma bovine calf sera are less expensive and in greater supply than fetal bovine sera.

Because of the unexpected results of the present invention, however, the ability of the sera blended at various ranges, and placed in a medium to provide for a composition secreted by an organism grown in the inventive medium is not a factor to be considered in the amount of fetal bovine sera to be blended with agamma bovine calf sera. Sera blended with fetal bovine sera and agamma bovine calf sera at the ranges described above provide for a composition about as well as sera comprised only of fetal bovine sera. In some instances the blended sera was superior to fetal bovine sera for producing a composition.

The types of organic products produced by organisms comprised within the invention include proteins, carbohydrates, nucleic acids, and other organic molecules. All of the foregoing can be characterized by methods known in the art to point out remarkable features of the compositions, the features being distinguishable from compositions not comprised in the present invention.

To illustrate the foregoing, an example is provided. The example, however, is for illustrative purposes, and is not to be used as a basis for limitation. Organisms are comprised of glycoproteins. The precise culture conditions used in any particular case to maintain or grow organisms will allow recovery of secreted glycoproteins of a desired structural integrity. A change in the glycosylation pattern can affect the purification procedures and the efficacy of a purified diagnostic/therapeutic protein. Therefore, organisms maintained or grown in the inventive sera, under any of the culture conditions previously discussed will secrete a protein having a unique glycosylation pattern.

Also, the present invention covers methods for the preparation of the inventive sera and the fetal bovine serum-containing media, and their use with a cellular line. Because of their increased importance to the scientific community, in the preferred embodiment of the present invention, a hybridoma cell line is placed in the presence of the inventive blended sera-containing culture media. All of the inventive blended sera-containing culture media and sera, and methods of production of same that have previously been discussed may be employed with a cellular line.

C. Uses of the Blended Sera

Hybridoma cell lines are artificially created to be employed in immunological studies and the production of diagnostic or therapeutic biologicals. A typical immune response results in the production of a broad spectrum of antibodies of varying affinities for an antigen. The antibodies directed toward a particular determinant will represent but a small proportion of the total antibody pool. If one could isolate a clone of B-cells, which are responsible for making a particular antibody of interest, a source of monospecific or monoclonal antibody would be available.

Techniques are now available for isolating and growing single B-lymphocytes for indefinite periods of time. This hybridoma technique procedure combines the unlimited division properties of a cancer cell with the monoclonal antibody production of a single B-lymphocyte. In practice, myeloma cells are fused with a pool of B-cells removed from a mouse previously immunized with the antigen of interest; agents (such as polyethylene glycol) are added to the mixture to promote fusion.

Since myeloma cells are themselves B-lymphocytes, a variant myeloma cell line that has lost the ability to make immunoglobulin is routinely employed in hybridoma selections. After fusing, the heterokaryotic hybrid cell undergoes a nuclear fusion and eventually results in antibody producing cells that can be selectively cloned and subsequently injected into an animal, where it grows as a myeloma tumor secreting monoclonal antibodies. The immunoglobulin molecules produced by a hybridoma are characteristic of the normal B-cell to which the malignant cell was fused. The resulting hybridoma population is screened using various immunological and biochemical techniques to identify the clone producing the monoclonal antibody of interest.

Monoclonal antibodies can be used as medical tools for the identification or destruction of specific antigens.

For example, it is known that subtle antigenic differences exist between the surfaces of malignant cells and normal cells. Monoclonal antibodies directed against cancer-related determinants might serve as effective weapons against cancer cells without harming normal cells. Monoclonal antibodies have also been described that can distinguish between human transplantation antigens, thus greatly simplifying the process of tissue matching for transplantation purposes. Monoclonal antibodies also appear promising as tools for use in routine diagnostics and in the treatment of a variety of diseases.

Currently, the most common and most economically important hybridomas are the mouse/mouse hybridomas. These can be prepared by using several mouse fusion partners. Examples of mouse fusion partners include the Sp2/0, P3x63-Ag8.653, NS-1, and FOX-NY cell lines. Other fusion partners exist and many are derived from the four listed above. Examples of additional hybridoma types include, but is not limited to mouse/rat; mouse/human; rat/rat; human/rat; human/human.

Many cell lines possess specific surface macromolecules that bind to complimentary receptor molecules on certain surfaces, thus promoting specific and firm adherence of the cell line to the surface. Certain of these macro-molecules are polysaccharide in nature and form a sticky meshwork of fibers called the glycocalyx. Monolayer culture is therefore the mode of culture common to these types of cell lines.

A monolayer culture suggests the inclusion of some type of substrate to which the cell lines can bind. Several examples of substrates include ceramics, carbohydrates, agarose, and proteins. The substrates can form flat surfaces, or they can form bead-like objects, suspended in a media, to which the cells attach.

Hybridoma cell lines, however, are unlike other cell lines that are able to adhere, or attach specifically to surfaces. Generally, hybridoma cell lines are non-attaching in nature. Therefore, this type of cell line must be grown suspended in a medium; suspension cultures are derived from cells which can survive and proliferate without attachment.

Although the present invention is preferably directed to hybridoma cell lines that are non-attaching, it must be understood that the present invention is not limited to this particular class of cellular line. Instead, the present invention covers cellular lines that are hybridoma in nature, but are attaching. Some hybridoma cell lines inherently attach to a surface, while others will attach to a surface under certain growth or incubation conditions.

The present invention includes the wide variety of nonhybridoma cellular lines that exist in nature or are manmade. The nonhybridoma cellular lines can be attaching or non-attaching in nature, depending upon the specific cellular line. Similar to the hybridoma cellular lines, nonhybridoma cellular lines may be inherently attaching or non-attaching, or will attach or non-attach upon certain growth or incubation conditions.

EXAMPLES

According to the present invention, it has been found that the following cellular lines could be embodied within the scope of the present invention. The scope of protection accorded to the present invention, however, should not be limited to the following cellular lines. The cellular lines are merely given as examples in order to allow one of ordinary skill in the art to identify other cellular lines that can be grown using the sera of the present invention. Descriptions of the following cellular lines were obtained from a catalog published by ATCC:

(1) CHO-K1 (ATCC CCL 61). The CHO-K1 cells were derived as a subclone from the parental CHO cell line initiated from a biopsy of an ovary of an adult Chinese hamster by T. T. Puck in 1957, (J. Exp. Med. 108: 945, 1958). The cells apparently lack the active gene form needed for proline synthesis and the block in the biosynthetic chain lies in the step converting glutamic acid to glutamic gammasemialdehyde (Genetics 55: 513, 1967). The cells have been used for the induction and isolation of nutritionally deficient mutants (Proc. Nat. Acad. Sci. 60: 1275, 1968).

(2) MDBK (ATCC CCL 22). The MDBK cell line was derived from a kidney of an apparently normal, adult steer, Feb. 18, 1957, by S. H. Madin and N. B. Darby, (Proc. Soc. Exp. Biol. Med., 98: 576, 1958). It is believed to be the first permanent cell line of a large domestic animal to be established.

(3) Vero (ATCC CCL 81). The Vero cell line was initiated from the kidney of a normal, adult, African green monkey on Mar. 27, 1962, by U. Y. Yasumura and Y. Kawakita at the Chiba University in Chiba, Japan (Nippon Rinsho 21: 1209, 1963). The Vero cell line has been employed extensively in virus replication studies and plaque assays.

(4) A549 (ATCC CCL 185). This cell line was initiated in 1972 by D. J. Girard et al. (J. Nat. Cancer Inst. 51: 1417–1423, 1973) through explant culture of lung carcinomatous tissue from a 58 year-old Caucasian male. Further studies M. Lieber et al., (Int. J. Cancer 17: 62–70, 1976) revealed that A549 cells could synthesize lecithin with a high percentage of desaturated fatty acids utilizing the cytidine diphosphocholine pathway.

(5) FOX-NY CD2 hybrid. The FOX-NY CD2 hybrid is a product of a fusion of FOX-NY cells (ATCC CRL 1732) and Robertsonian RFB BF/Dn Mouse spleen cell produced by HyClone Laboratories, Inc. The myeloma cell line designated FOX-NY was derived by R. T. Taggert, et al. from the nonimmunoglobulin producing strain NS-1 (ATCC TIB 18). The FOX-NY is suitable for producing murine hybridomas using either the adenosine phosphoribosyltransferase (APRT)+ or hypoxanthine phosphoribosyltransferase (HPRT)+ culture selection method and is comparable to other myeloma lines used in the fusion process with respect to growth properties, fusion frequency and stability of resulting hybrids.

(6) Sp2/0 hybrid. The Sp2/0 hybrid is a product of a fusion of an Sp2/0-Ag14 myeloma (ATCC CRL 1581) and Balb/C Mouse spleen cell produced at HyClone Laboratories, Inc. The Sp2/0-Ag14, developed by M. Schulman, C. Wilde and G. Kohler, is a hybridoma variant used in the fusion process for obtaining cell lines (hybridomas) which produce antibody of a desired specificity (Nature 276:269–270, 1978). Sp2/0 does not synthesize or secrete any immunoglobulin chains, is resistant to 8-azaguanine at 20 ug/ml and does not survive in HAT containing media.

(7) P3X6-3Ag8.653 (ATCC CRL 1580). P3X63-Ag8.653, developed by J. Kearney et ill., is a subclone of the mouse myeloma cell line P3X63Ag8 (ATCC TIB 9) that has lost the ability to produce immunoglobulin heavy or light chains (J. Immunol. 123: 1548–1550, 1979).

(8) HBAE. HBAE cells were isolated from Bovine Aorta Endothelial tissue as a primary culture cell line by HyClone Laboratories, Inc.

(9) MRC-5 (ATCC CCL 171). The MRC-5 cell line was derived from normal lung tissue of a 14 week-old male fetus by J. P. Jacobs in September of 1966 (Nature 227: 168–170, 1970). Comparative studies (Proc. Symp. Human Diploid Cells, Yugoslav Acad. Sci. Arts, Zagreb., pp. 43–55, 1970) showed that MRC-5 cells replicate more rapidly and are less sensitive to adverse environmental factors than WI-38 cells (ATCC CCL 75).

(10) NS-1 cells: (ATCC T1B18) in DMEM, 90% (Dulbecco's Modified Eagle's Medium) (HyClone catalog #B10-1006-CC); HyClone Control Fetal Bovine Serum, 10% (HyClone catalog #1114-D). NS-1 is a non-secreting clone of P3X63Ag8 (ATCC T1B 9). NS-1 cells are resistant to $10^{-4}$M 8-azaguanine, do not grow in HAT medium and have been used extensively in cell fusion studies. (Eur. J. Immounol. 6: 511, 1976), (J. Mol. Biol. 90: 691, 1974).

(11) CEM cells: (ATCC CCL 119) in RPMI 1640, 90% (Roswell Park Memorial Institute formulation #1640) (HyClone catalog #B10-0304-CC); HyClone Control Fetal Bovine Serum, 10%. CEM cells are a T lymphoblastoid cell line derived by G. E. Foley et al. (Cancer 18: 522–529, 1965). Cells were obtained in November, 1964 from peripheral blood buffy coat of a four-year-old caucasian female with acute lymphoblastic leukemia. The cells are apparently free of virus-like particles as determined by electroll microscopy, (Cancer 19: 1725–1742, 1966) and apparently do not synthesize immunoglobulins and are karyotypically "near-diploid" (Exp. Cell Res. 40: 197–200, 1965).

(12) MOLT-4 cells: (ATCC CRL 1582) in RPMI 1640, 90%; HyClone Control Fetal Bovine Serum, 10%. MOLT-4 is a suspension culture derived from the peripheral blood of a 19 year-old male with acute lymphoblastic leukemia in relapse it is reportedly a stable T-cell leukemia; the cells bind with sheep erythrocytes to form rosettes. The MOLT-4 cell line was tested weekly by the Hoechst method for a three month period. All test results were negative and the line can be considered to be cured.

All stock cells used for growth promotion and other studies were maintained in the appropriate basal culture medium and HyClone Control Fetal Bovine Serum (HyClone Catalog#1114-D). Non-attaching cell lines were rinsed twice via centrifugation (400 xg for 10 minutes) and resuspended in cell culture medium without serum. Attaching cell lines were detached from the flask via trypsination in 0.05% trypsin (GIBCO catalog#610-5095AE) and rinsed as described above.

Cell density was determined by cell counts using a hemacytometer. Plating density for the non-attaching cell lines was $2.5 \times 10^4$ cells/ml. Plating density for the attaching cell lines was $5 \times 10^4$ cells/flask. Culture flasks used were the Costar R T-25 (catalog#3025).

Environmental conditions wherein the hybridoma cell line in the presence of fetal bovine serum-containing media is incubated comprise the step of inducing a $CO_2$ atmosphere in the range from about ambient levels to about ten percent (10%).

A further step is also comprised within the present invention of incubating the hybridoma cell line in the presence of fetal bovine-containing media at a temperature in the range from about 4° C. to about 42° C. In the most preferred embodiment of the present invention the incubation temperature is at a temperature range from about 35° C. to about 40° C.

The following examples are exemplary of novel media for the maintenance and promotion of hybridoma cell lines that have been made and accomplished using the present invention, but are given by way of illustration only. In these examples, various components were incorporated into a medium and the medium was used to maintain and promote the growth of a hybridoma cell line.

Example 1

The media of the present invention blended sera was prepared in accordance with the present invention using non-iron-supplemented agamma bovine calf serum that was added to fetal bovine serum at a ratio of 9 parts agamma bovine calf serum to one part of fetal bovine serum. The agamma bovine calf serum was AlphaCalf and it was obtained from HyClone Laboratories, Inc. The agamma bovine calf serum was characterized in that it had a higher lipid concentration than the lipid concentrations found in other agamma bovine calf sera.

After the agamma bovine calf serum was added to the fetal bovine serum, the iron level of the mixture was determined as per manufacturer's instructions using a SIGMA iron and iron-binding capacity kit (Catalogue #565-B). The mixture was then supplemented to 70% of the iron-binding capacity of the mixture. The mixture was filter-sterilize& through 3 Millipore Durapore 0.1 micron pore-rated filters (Catalog #CVVL 73TP3) arranged in series.

Next, a medium for maintaining or promoting the growth of a cellular line was prepared. The first step of the preparation required the preparation of a fetal bovine containing blend. Then, the next step of the experiment required the addition of a basal culture medium to the serum blend. Specifically, Dulbecco's Modified Eagle's Medium TM was added to the blended serum.

Finally, a serum for use in a medium for promoting the growth of a hybridoma cell line was prepared. In addition to the serum and the medium previously prepared, the Sp2/0 hybridoma cell line was placed in communication with the solution.

The Sp2/0 hybridoma cell line was maintained in a 90% DMEM and 10% HyClone Control Fetal Bovine Serum solution before the growth promotion testing. At the time of the testing, the cells were centrifuged at 400 (x)g for 10 minutes and resuspended in a DMEM solution. From the resuspended solution having a cell density of $2.5 \times 10^4$ cells/ml, 5.7 ml was extracted and added to 0.3 ml of the blended sera. The latter solution was placed in a Costar R T-25 (catalog#: 3025) flask and incubated in a 5% $CO_2$ atmosphere at 37° C.

The cell culture was then observed on each of five successive days after culture initiation and counted. On each day, 0.2 ml of the cell/growth medium solution was aseptically removed from the culture flask and added to an Acuvette (Coulter catalog #7546472, 1000×35 ml vial) containing 20 ml of an isotonic buffer solution (Coulter Isoton II, catalog #8546720). This dilute cell/buffer solution was then counted using a Coulter ZM Cell Counter.

In order to determine the growth promotion sapabilities of the medium used to grow the Sp2/0 hybridoma cell line, various ratios of the agamma bovine calf serum and the fetal bovine serum were blended. The results of the Sp2/0 hybridoma cell lines grown under the foregoing procedures at the various ratios are indicated in FIG. 1.

The blended sera treated Sp2/0 hybrid cells exhibited a constant trend of cell growth comparable to fetal bovine serum treated Sp2/0 hybrid cells. At 5% serum concentration, the blended sera treated cells averaged $1.06 \times 10^6$ cells/flask, the fetal bovine serum treated cell averaged $1.02 \times 10^6$ cells/flask, and the agamma bovine calf serum treated cells averaged $7.90 \times 10^5$ cells/flask.

Example 2

Figure 2:
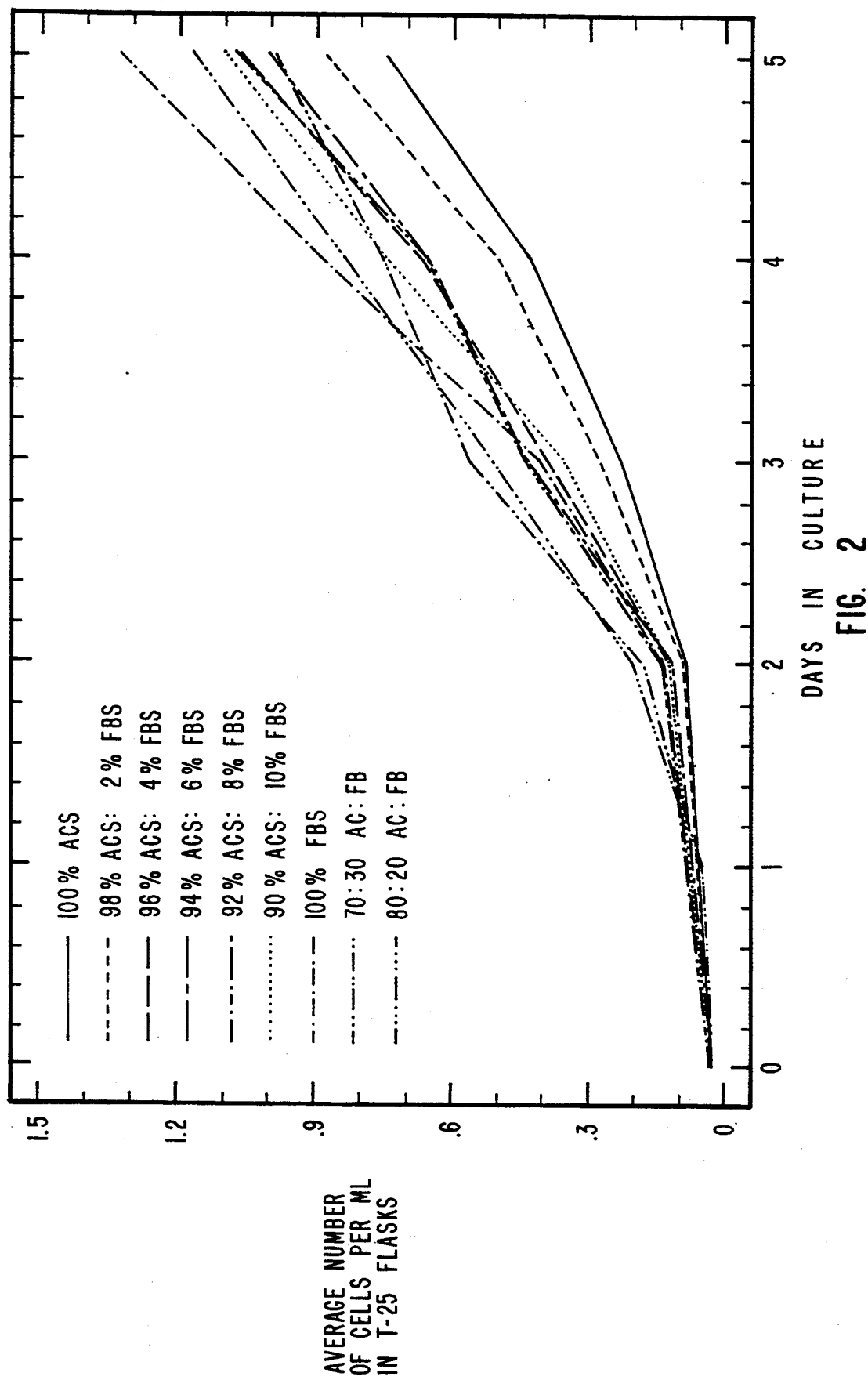
FIG. 2 shows a chart that compares the growth over time of the Sp2/0 cellular line in a medium containing various inventive serum blends. The medium has 10% serum in DME medium.

A serum for use in a medium for promoting the growth of a hybridoma cell line was prepared according to example 1, except that the concentration of the blended sera in the DMEM solution was 10%. The results of the Sp2/0 hybridoma cell lines grown under the foregoing procedures at the various ratios are indicated in FIG. 2.

At the 10% blended sera concentration, the blended sera treated cells averaged $1.14 \times 10^6$ cells/flask, the fetal bovine serum treated cells averaged $1.08 \times 10^6$ cells/flask, and the agamma bovine calf serum treated cells averaged $8.70 \times 10^5$ cells/flask. Therefore, the results indicate that blended sera treated cells exhibit a constant trend of cell growth comparable to fetal bovine serum treated cells.

Example 3

Figure 3:
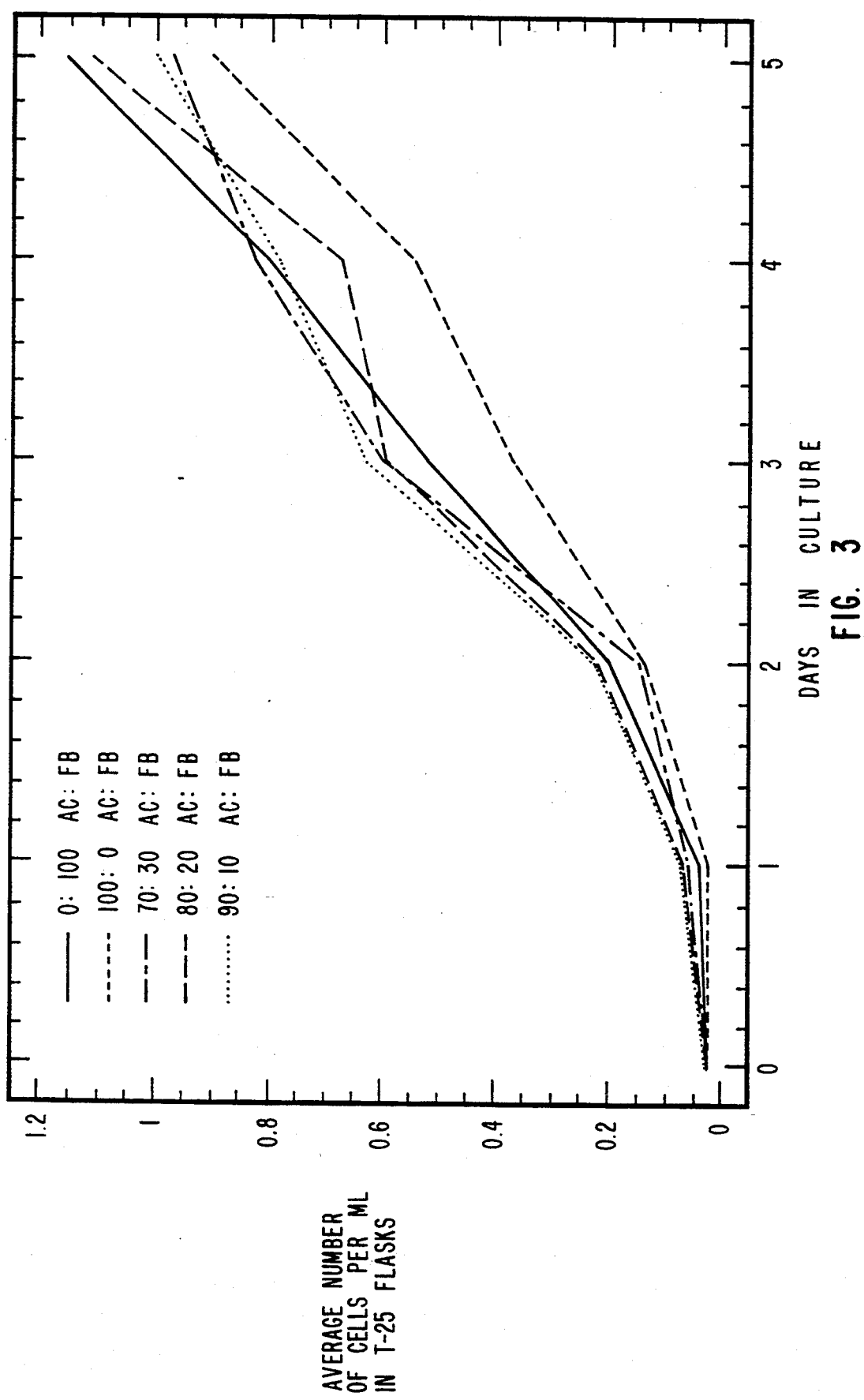
FIG. 3 shows a chart that compares the growth over time of the Sp2/0 cellular line in a medium containing various inventive serum blends. The medium has 20% serum in DME medium.
Figure 4:
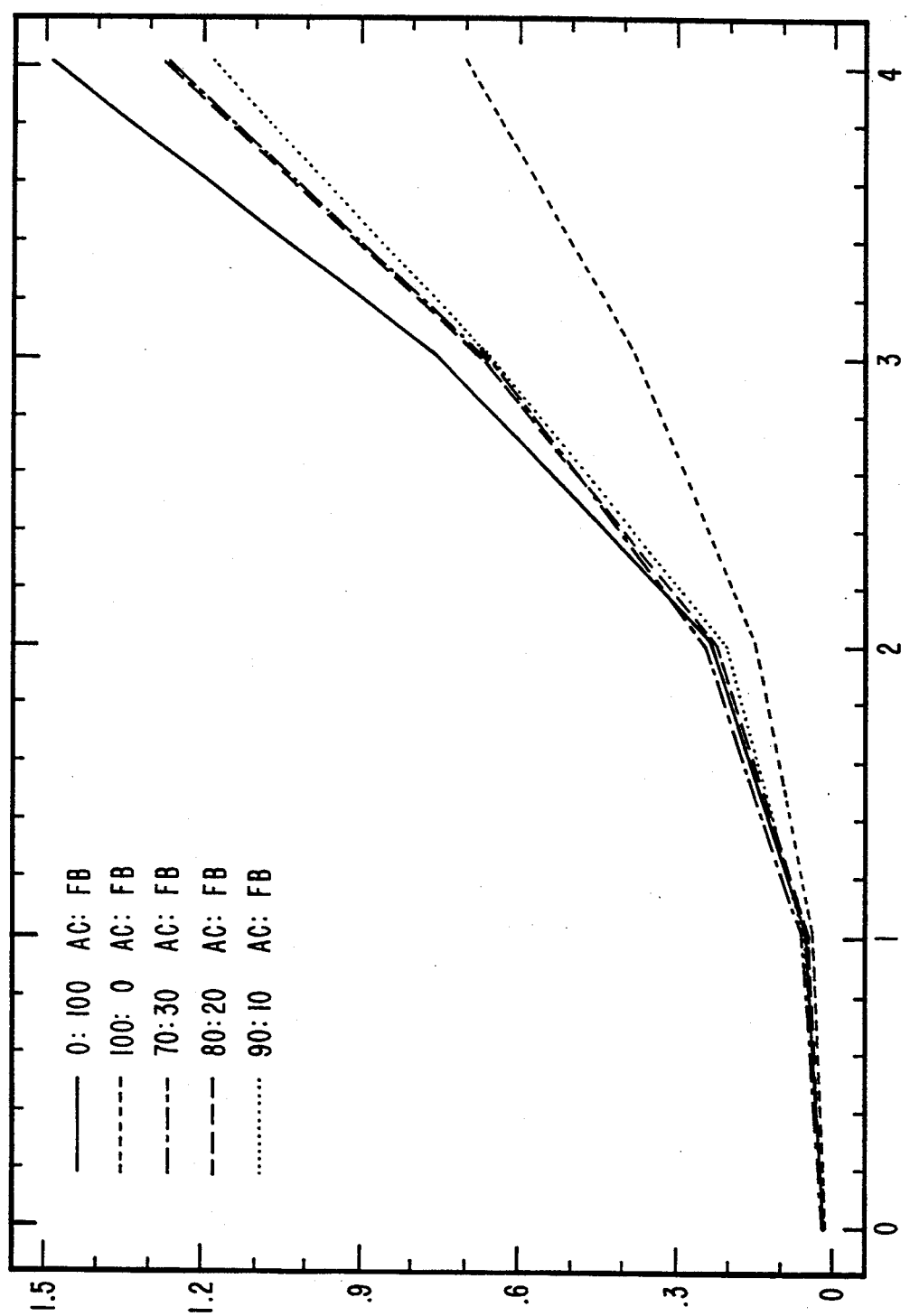
FIG. 4 shows a chart that compares the growth over time of the FOX-NY CD2 cellular line in a medium containing various inventive serum blends. The medium has 5% serum in DME medium.

A serum for use in a medium for promoting the growth of a hybridoma cell line was prepared according to example 1, except that the concentration of the blended sera in the DMEM solution was 20%. The results of the Sp2/0 hybridoma cell lines grown under the foregoing procedures at the various ratios are indicated in FIG. 3.

At 20% serum concentration, the blended sera treated cells averaged $1.14 \times 10^6$ cells/flask, the fetal bovine serum treated cells averaged $1.08 \times 10^6$ cells/flask, and the agamma bovine calf serum treated cells average $8.70 \times 10^5$ cells/flask. At 20% serum concentration there seemed to be an inhibitory effect of the serum on cell growth promotion. The results indicate that blended sera treated cells exhibit a constant trend of cell growth comparable to fetal bovine serum treated cells. In some ranges the growth trend of the blended sera treated cells is actually superior to the growth trend of the fetal bovine treated cells.

Example 4

Figure 6:
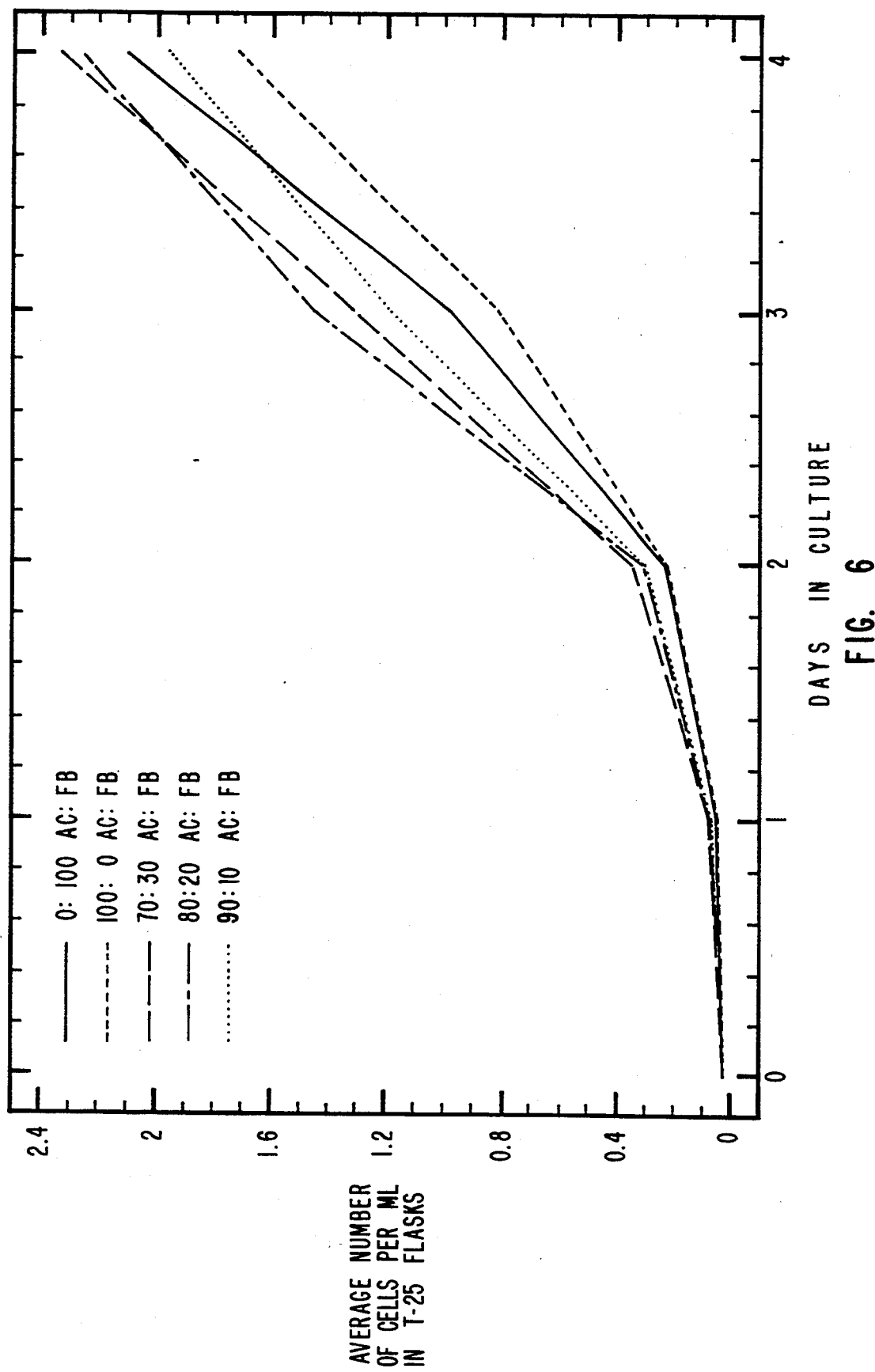
FIG. 6 shows a chart that compares the growth over time of the FOX-NY CD2 cellular line in a medium containing various inventive serum blends. The medium has 20% serum in DME medium.

A serum for use in a medium for promoting the growth of a hybridoma cell line was prepared according to example 1, except that the FOX-NY CD2 hybrid cell line was employed and the cell line was originally maintained in an 85% DMEM/15% HyClone Control Fetal Bovine Serum solution. The results of the FOX-NY CD2 hybrid cell line grown under the foregoing procedures at the various ratios are indicated in FIG. 6.

Similar to the Sp2/0 hybrid cell line, the blended sera treated FOX-NY CD2 hybrid cells exhibited a constant trend of cell growth comparable to fetal bovine serum treated FOX-NY CD2 hybrid cells. At 5% serum concentration, blended sera treated cells averaged $1.17 \times 10^6$ cells/flask, fetal bovine serum treated cells averaged $1.48 \times 10^6$ cells/flask, and agamma bovine calf serum treated cells averaged $7.10 \times 10^5$ cells/flask. Therefore, the results indicate that blended sera treated cells exhibit a constant trend of cell growth comparable to fetal bovine serum treated cells.

Example 5

Figure 5:
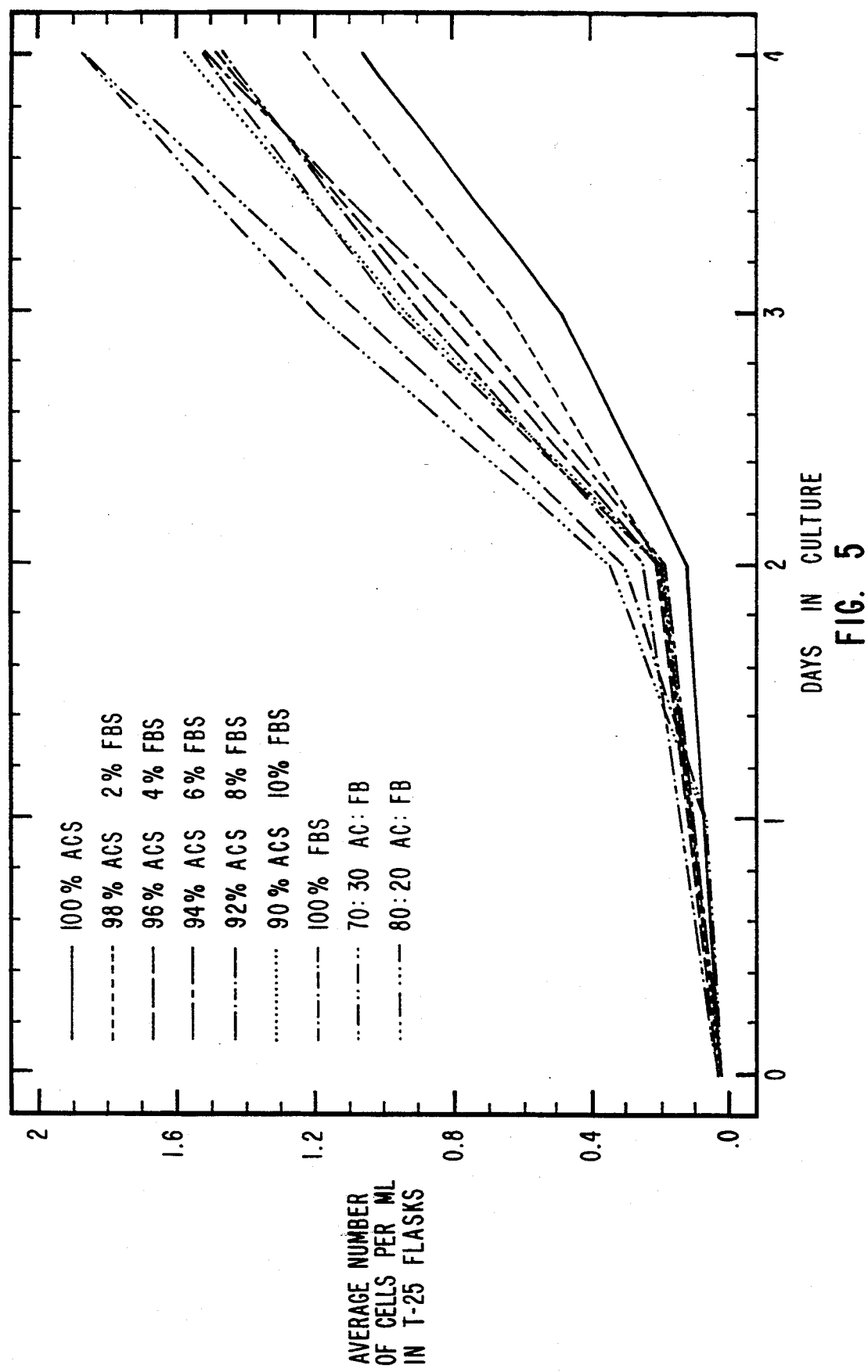
FIG. 5 shows a chart that compares the growth over time of the FOX-NY CD2 cellular line in a medium containing various inventive serum blends. The medium has 10% serum in DME medium.

A serum for use in a medium for promoting the growth of a hybridoma cell line was prepared according to example 4, except that the concentration of the blended sera in the DMEM solution was 10%. The results of the FOX-NY CD2 hybrid cell line grown under the foregoing procedures at the various ratios are indicated in FIG. 5.

At 10% serum concentration, blended sera treated cells averaged $1.97 \times 10^6$ cells/flask. At the same serum concentration, fetal serum treated cells averaged $1.97 \times 10^6$ cells/flask, and agamma bovine calf serum treated cells averaged $1.20 \times 10^6$ cells/flask. Therefore, the results indicate that blended sera treated cells exhibit a constant trend of cell growth comparable to fetal bovine serum treated cells.

Example 6

A serum for use in a medium for promoting the growth of a hybridoma cell line was prepared according to example 4, except that the concentration of the blended sera in the DMEM solution was 20%. The results of the FOX-NY CD2 hybrid cell line grown under the foregoing procedures at the various ratios are indicated in FIG. 6.

At 20% serum concentration blended sera treated cells averaged $1.95 \times 10^6$ cells/flask, fetal bovine serum treated cells averaged $2.10 \times 10^6$ cells/flask, and agamma bovine calf serum treated cells averaged $1.72 \times 10^6$ cells/flask. Although the trend among cell culturists is to minimize serum concentrations used in cell culture, 10% serum concentration is the current standard used in most cell culture media compositions. Interestingly, blended sera used at this concentration exhibit growth promotion characteristics almost identical to fetal bovine serum.

Example 7

Figure 7:
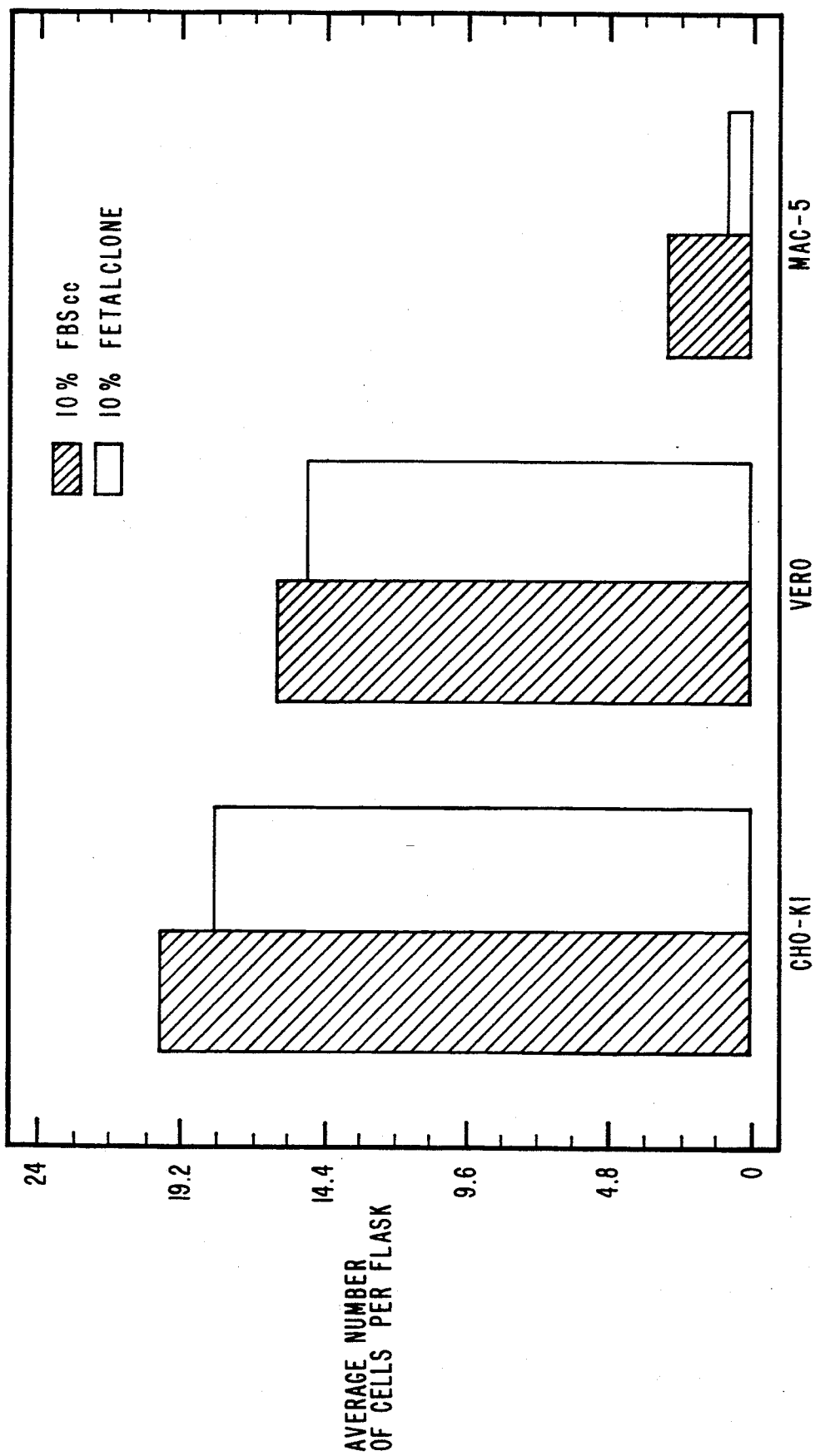
FIG. 7 shows a chart that illustrates the growth promotion studies conducted on various attaching cell lines. The sera compared comprise a blend of 90% fetal bovine sera, and 10% agamma bovine calf sera and a control medium containing 10% HyClone Control FBS. The medium has 10% serum in DMEM medium.

Example 7 refers to growth promotion studies conducted on various attaching cell lines. Specifically, the CHO-K1 and Vero cell lines were tested for the effect blended sera had on their cell growth in comparison to a control solution of fetal bovine serum. Reference to FIG. 7 is made with regard to the results of the testing.

In the preparation of the growth promotion, the tested cell lines were maintained in serum blended media comprising 0.3 ml of blended sera media and 5.7 ml of Ham's F12 media. The cells were maintained in Costar ® T-25 culture flasks. Cell cultures were then terminated four to five days after initiation for the purpose of cell counting. The cell counts were performed using a Coulter ZM cell counter. The medium was removed from the culture flasks and discarded. The cell monolayer was rinsed in a 0.1M phosphate buffered saline (PBS) solution for five minutes. The PBS was removed and discarded. One ml of 0.05% trypsin was added to the PBS-rinsed cell monolayer and the flasks were incubated at 37° C., in a 5% $CO_2$ atmosphere until the cell monolayer was dissociated from the growth surface of the flasks.

Upon cell dissociation, 0.2 ml of the cell/trypsin solution was removed from the flask and dispensed into an Acuvette (Coulter Catalog #7546472, 1000×35 ml vial) containing 20 ml of an isotonic buffer solution (Coulter Isoton II, Catalog #8546720). This dilute cell/buffer solution was then counted using Coulter ZM Cell Counter.

Results of the testing indicated that the CHC,-K1 and Vero cell lines grew at about the same rate whether grown in blended sera or the control solution of fetal bovine serum. After five days, the CHO-K1 cell line averaged $1.99 \times 10^6$ cells/ml in the control solution of fetal bovine serum and about $1.8 \times 10^6$ cells/ml in the blended sera. After five days, the Vero cell line averaged $1.6 \times 10^6$ cell/ml in the control solution of fetal bovine serum and about $1.5 \times 10^6$ cells/ml in the blended sera.

Example 8

Figure 8:
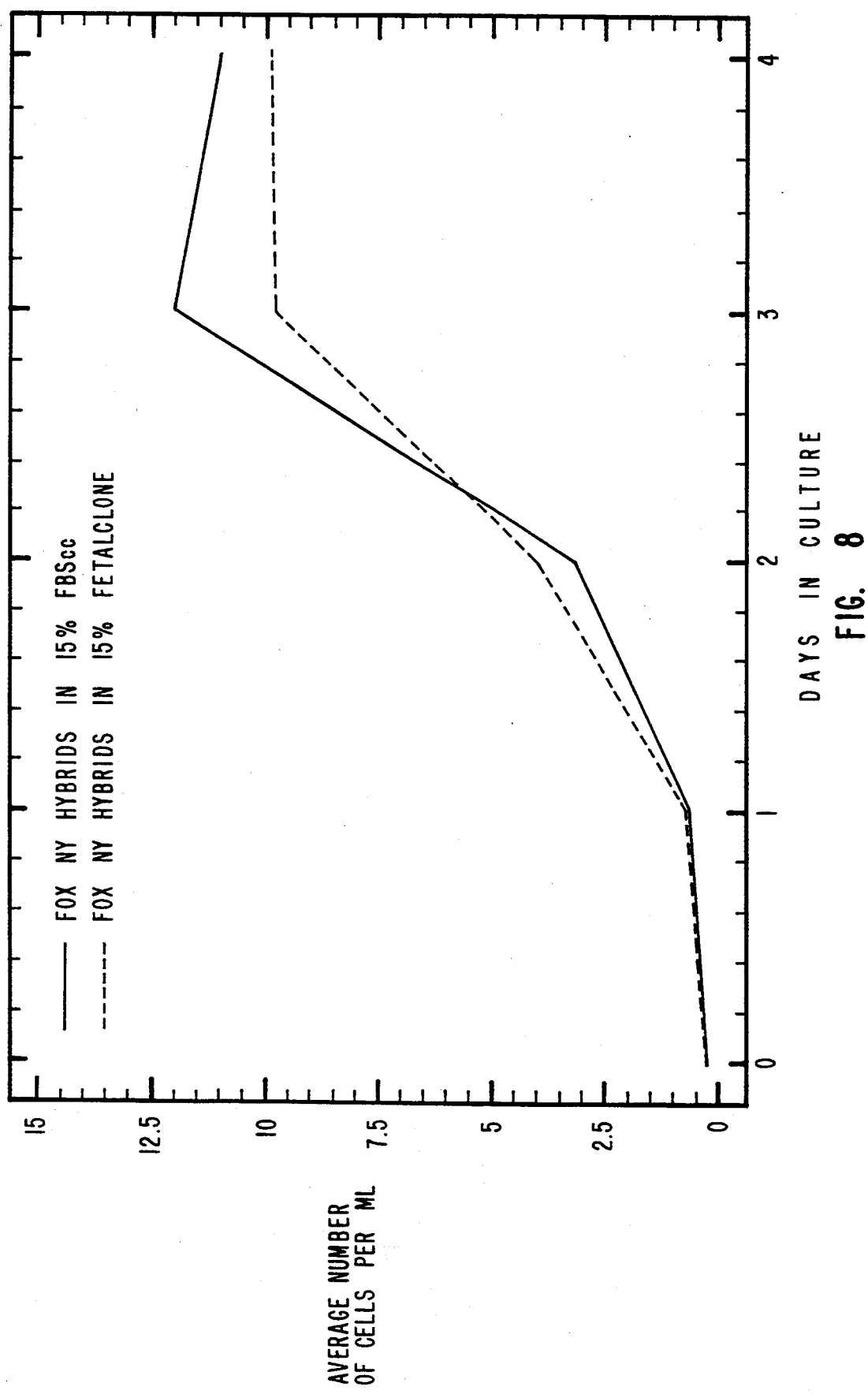
FIG. 8 shows a chart that illustrates the growth promotion studies conducted on FOX NY CD2 hybrid cellular line. The serums compared are the inventive serum blends and a control solution of fetal bovine serum. The medium has 15% serum in DMEM medium.

Example 8 refers to growth promotion studies conducted on the FOX-NY CD2 cell lines, tested for the effect blended sera had on its cell growth in comparison to a control solution of fetal bovine serum. The FOX-NY CD2 cell line was grown according to the conditions in Example 1, except that the blended sera and HyClone Control Fetal Bovine Serum solution comprised fifteen percent (15%) of the medium. Reference to FIG. 8 is made with regard to the results of the testing.

As in Example 4, the FOX-NY CD2 cell line grew approximately at the same rate in either serum employed. On day 4, about $1.1 \times 10^6$ cells/ml were obtained in the HyClone Control Fetal Bovine Serum media. Similarly, about $9.90 \times 10^5$ cells/ml were obtained in the blended sera.

Example 9

Example 9 refers to the plating efficiency of A549 cell lines. A549 stock cells (ATCC CCL 185) were maintained and rinsed as described in Example 1. The cells were resuspended in media containing 4% and 10% of the blended sera at two cell seeding concentrations; 200 cells/5 ml and 400 cells/5 ml. The cells were also resuspended in media containing 4% and 10% of HyClone Control Fetal Bovine Serum (HyClone catalog #1114-D) at the two cell seeding concentrations. Five ml of the cell suspension was added to each well of a Costar 6-2311 Tissue Culture Cluster (catalog #3406). The plates were incubated at 37° C. and in a 5% $CO_2$ atmosphere for 10 days.

On day 10 the culture medium was removed and the cells were stained with 1.0 ml of crystal violet solution (Baxter Scientific Products catalog #B1091-8) for five minutes. The stain was removed and the monolayers were rinsed three times with 5 ml 0.1M PBS per well. The cell colonies were counted and compared with the number of cell colonies which should have been generated. The percent plating efficiency was calculated as follows:

$$\% \text{ plating efficiency} = \frac{\text{number of colonies counted}}{\text{number of cells plated}}$$

Figure 9:
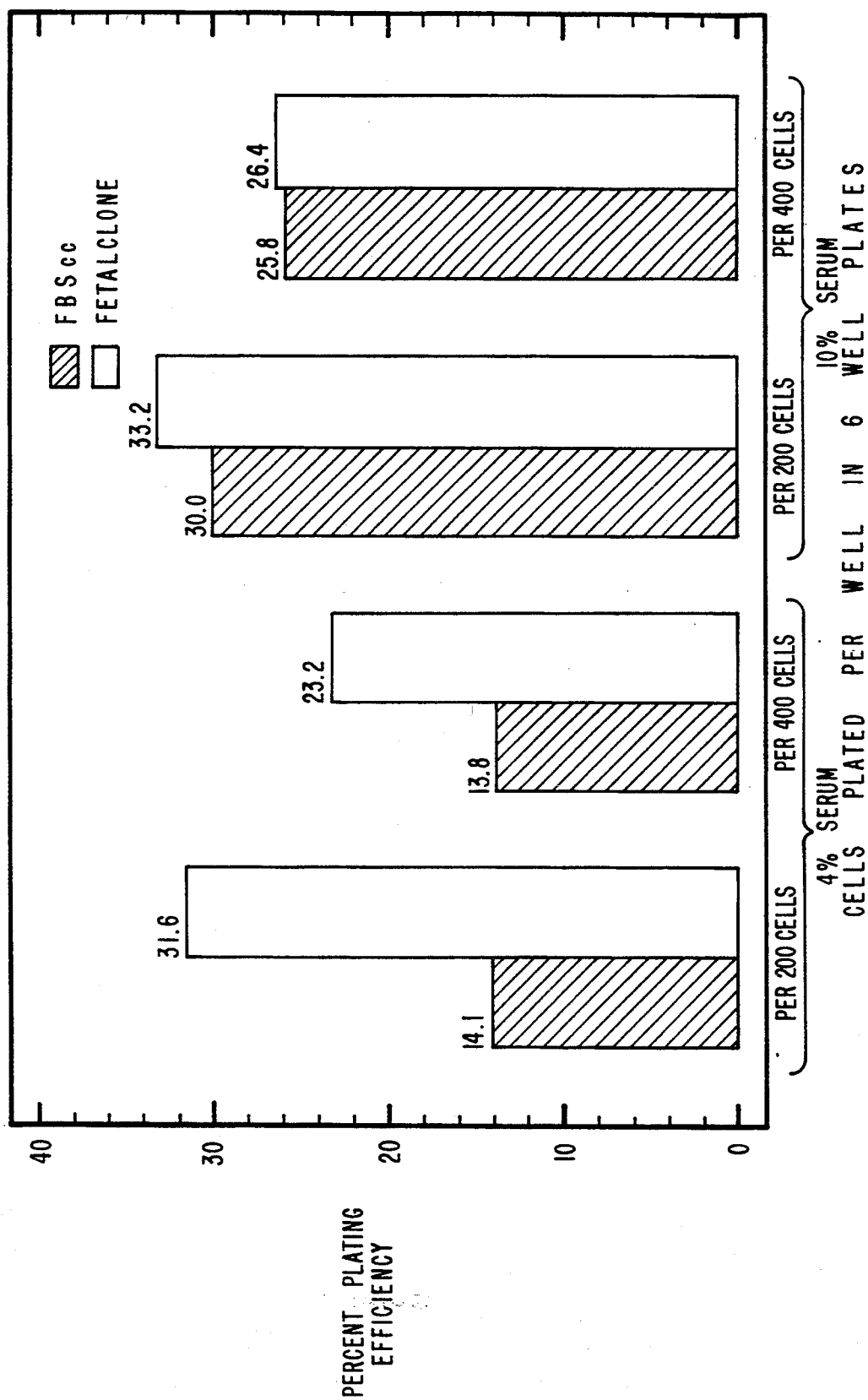
FIG. 9 shows the plating efficiency of A549 cells in media having different serum concentrations. Comparisons are made of the inventive serum blends and a control solution of fetal bovine serum.

The results are indicated in FIG. 9, and they indicate that for a medium employing ten percent (10%) serum, A549 cells grow as well in blended sera or fetal bovine serum-containing medium without regard to the initial number of cells plated. When 200 cells were plated, about 30% and 33.2% plating efficiency was obtained for the control solution of fetal bovine serum and blended sera respectively. When 400 cells were plated, about 25.8% and 26.4% plating efficiency was obtained for the control solution of fetal bovine serum and blended sera respectively.

Example 10

Example 10 refers to the cloning efficiency of the FOX-NY CD2 cell line. FOX-NY CD2 stock cells were maintained and rinsed as described in Example 1. The cells were resuspended in medium containing 15% of the blended sera at a cell concentration of 3 cells per 0.2 ml. Cells were also resuspended in medium containing 15% of HyClone Control Fetal Bovine Serum (catalog #1114-D) at a cell concentration of 3 cells per 0.2 ml. The cell suspension was added to a Costar 96-well Tissue Cluster (catalog #3596) such that each well should contain 3 cells (0.2 ml per well). The 96-well plates were incubated at 37° C. in a 5% $CO_2$ atmosphere for seven days.

On the day 7, the plates were observed microscopically and the number of cell colonies were counted and compared to the number of colonies that should have been generated. The Percent Cloning Efficiency was expressed as follows:

$$\% \text{ cloning efficiency} = \frac{\text{number of colonies counted}}{\text{number of cells plated}}$$

Figure 10:
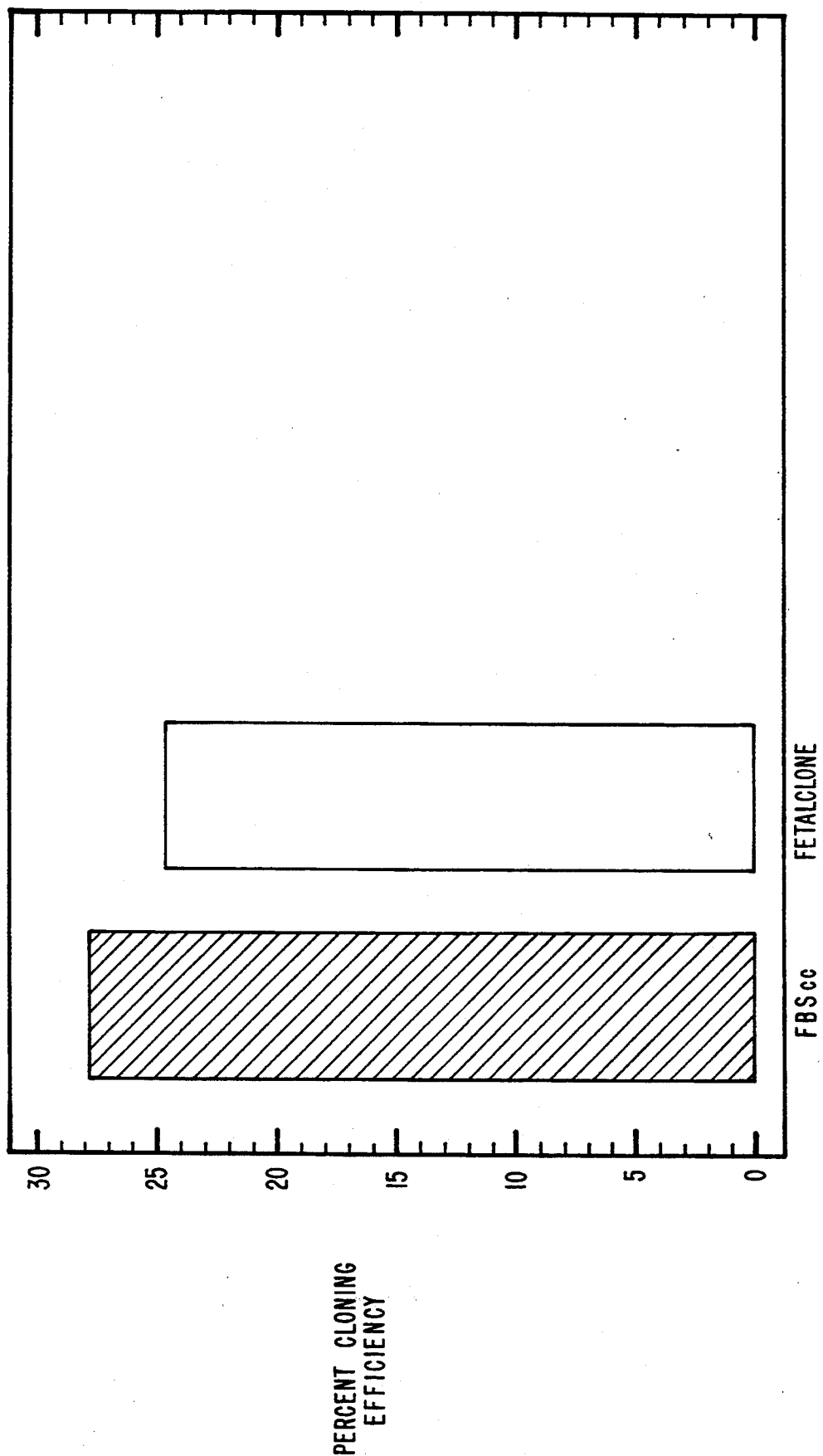
FIG. 10 shows the cloning efficiency of FOX-NY hybrids in media comprising either the inventive serum blends or a control solution of fetal bovine serum.

The results are indicated in FIG. 10, and they indicate that for a medium employing 15% serum, FOX-NY CD2 cells cloned as well in the blended serum or fetal bovine serum-containing media without regard to the initial number of cells plated. When 3 cells were plated, about 27.8% and 24.6% cloning efficiency was obtained for the control solution of fetal bovine serum and the inventive blended serum, respectively.

Example 11

Figure 11:
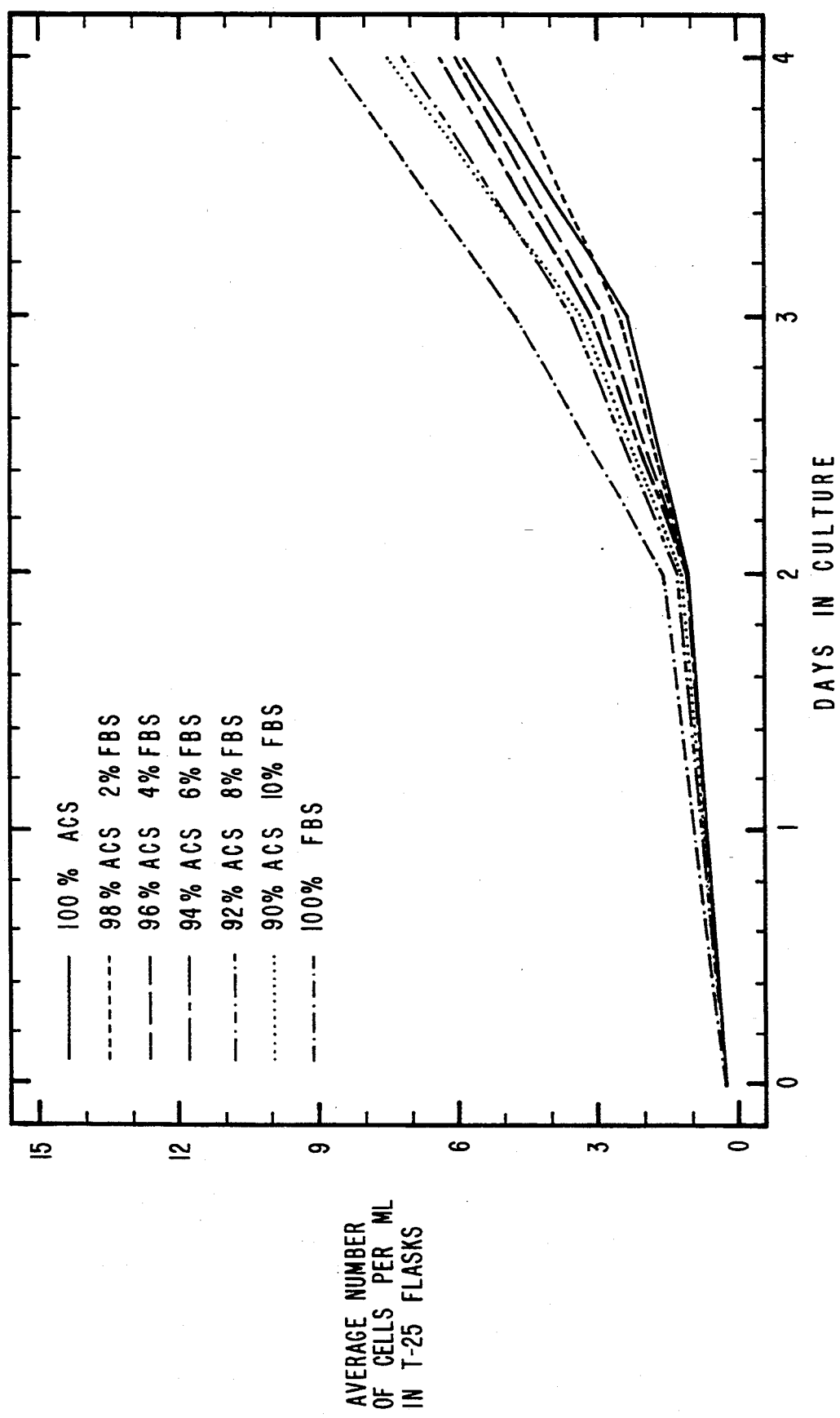
FIG. 11 shows a chart which compares the growth over time of the NS-1 cellular line in a medium containing various inventive serum blends. The medium has 5% serum in DME medium.

A serum for use in a medium for promoting the growth of a hybridoma cell line was prepared according to example 1, except that the NS-1 hybrid cell line was employed. The results of the NS-1 hybrid cell line grown under the foregoing procedures at the various ratios are indicated in FIG. 11.

At 5% serum concentration, blended sera treated cells averaged about $7.44 \times 10^5$ cells/flask, fetal bovine serum treated cells averaged about $8.69 \times 10^5$ cells/flask, and agamma bovine calf serum treated cells averaged $5.83 \times 10^5$ cells/flask. Similar to the Sp2/0hybrid cell line, the blended sera treated NS-1 hybrid Cells exhibited a constant trend of cell growth comparable to fetal bovine serum treated NS-1 hybrid cells.

Example 12

Figure 12:
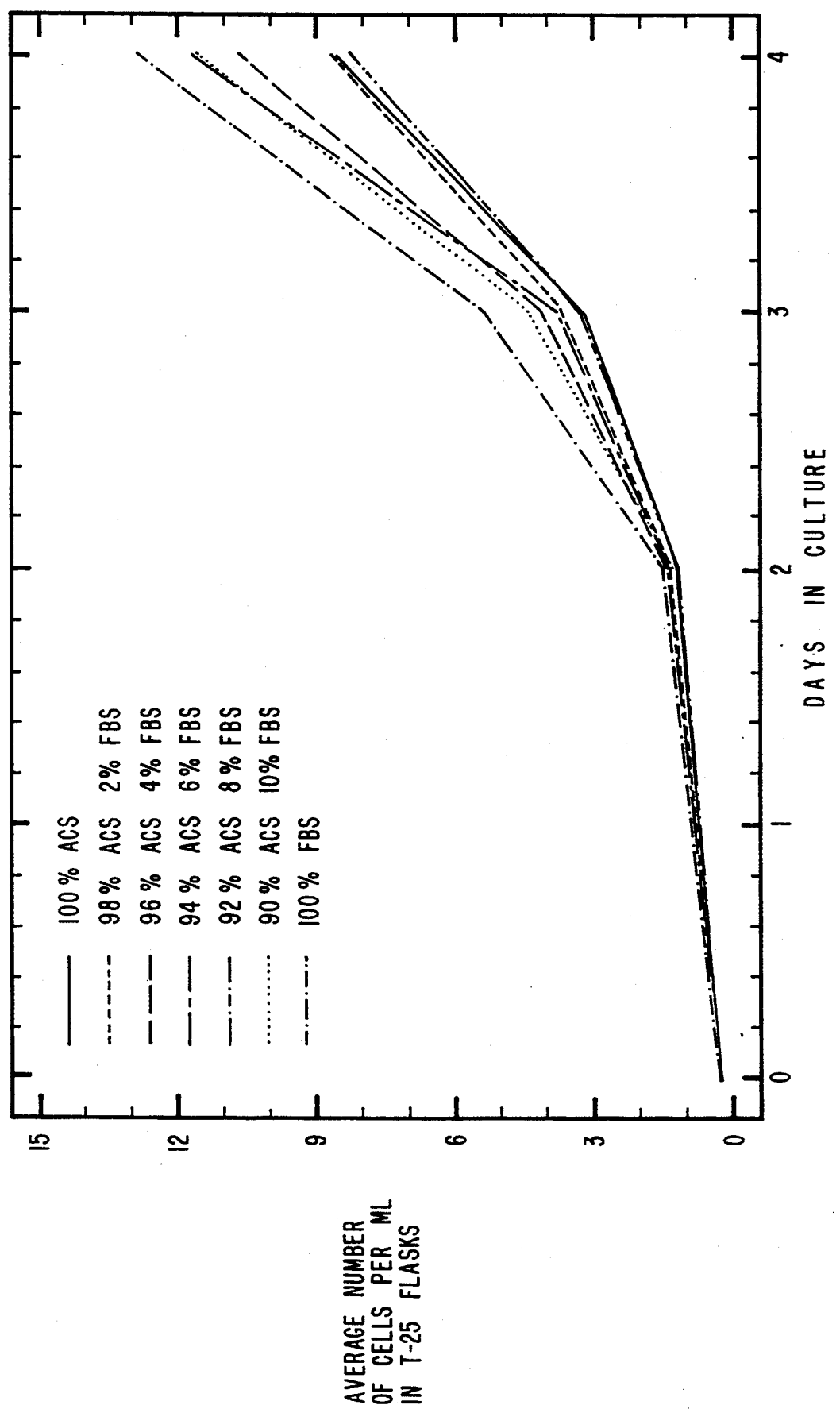
FIG. 12 shows a chart which compares the growth over time of the NS-1 cellular line in a medium containing various inventive serum blends. The medium has 10% serum in DME medium.

A serum for use in a medium for promoting the growth of a hybridoma cell line was prepared according to example 11, except that the NS-1 hybrid cell line was grown in a media containing ten percent (10%) of the serum blend. The results of the NS-1 hybrid cell line grown under the foregoing procedures at the various ratios are indicated in FIG. 12.

At 10% serum concentration, blended sera treated cells averaged about $1.15 \times 10^6$ cells/flask, fetal bovine serum treated cells averaged about $1.28 \times 10^6$ cells/flask, and agamma bovine calf serum treated cells averaged $8.53 \times 10^5$ cells/flask. Similar to the NS-1 hybrid cell line of FIG. 13, the blended sera treated NS-1 hybrid cells exhibited a constant trend of cell growth comparable to fetal bovine serum treated NS-1 hybrid cells.

Example 13

Figure 13:
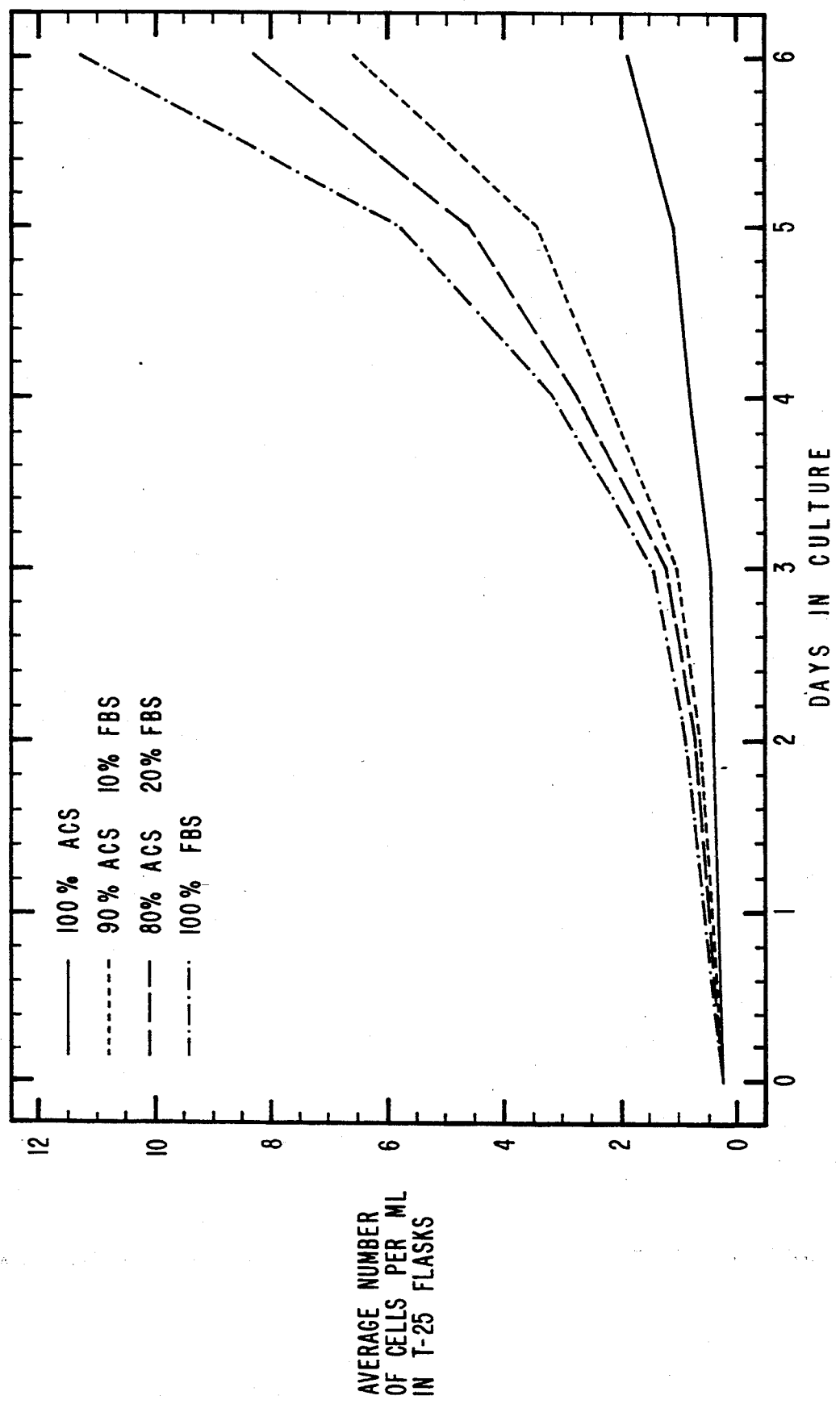
FIG. 13 shows a chart which compares the growth over time of the CEM cellular line in a medium containing various inventive serum blends. The medium has 10% serum in RPMI 1640 medium.

A serum for use in a medium for promoting the growth of a hybridoma cell line was prepared according to example 1, except that the CEM cell line was employed. In addition, the CEM cell line was placed in a media containing RPMI 1640 and a serum blend at a concentration of ten percent (10%). The results of the CEM cell line grown under the foregoing procedures at the various ratios are indicated in FIG. 13.

At 10% serum concentration, blended sera treated cells averaged about $8.26 \times 10^5$ cells/flask, fetal bovine serum treated cells averaged about $1.12 \times 10^6$ cells/flask, and agamma bovine calf serum treated cells averaged $1.87 \times 10^5$ cells/flask. Similar to the Sp2/0 hybrid cell line, the blended sera treated CEM cells exhibited a constant trend of cell growth comparable to fetal bovine serum treated CEM cells.

Example 14

Figure 14:
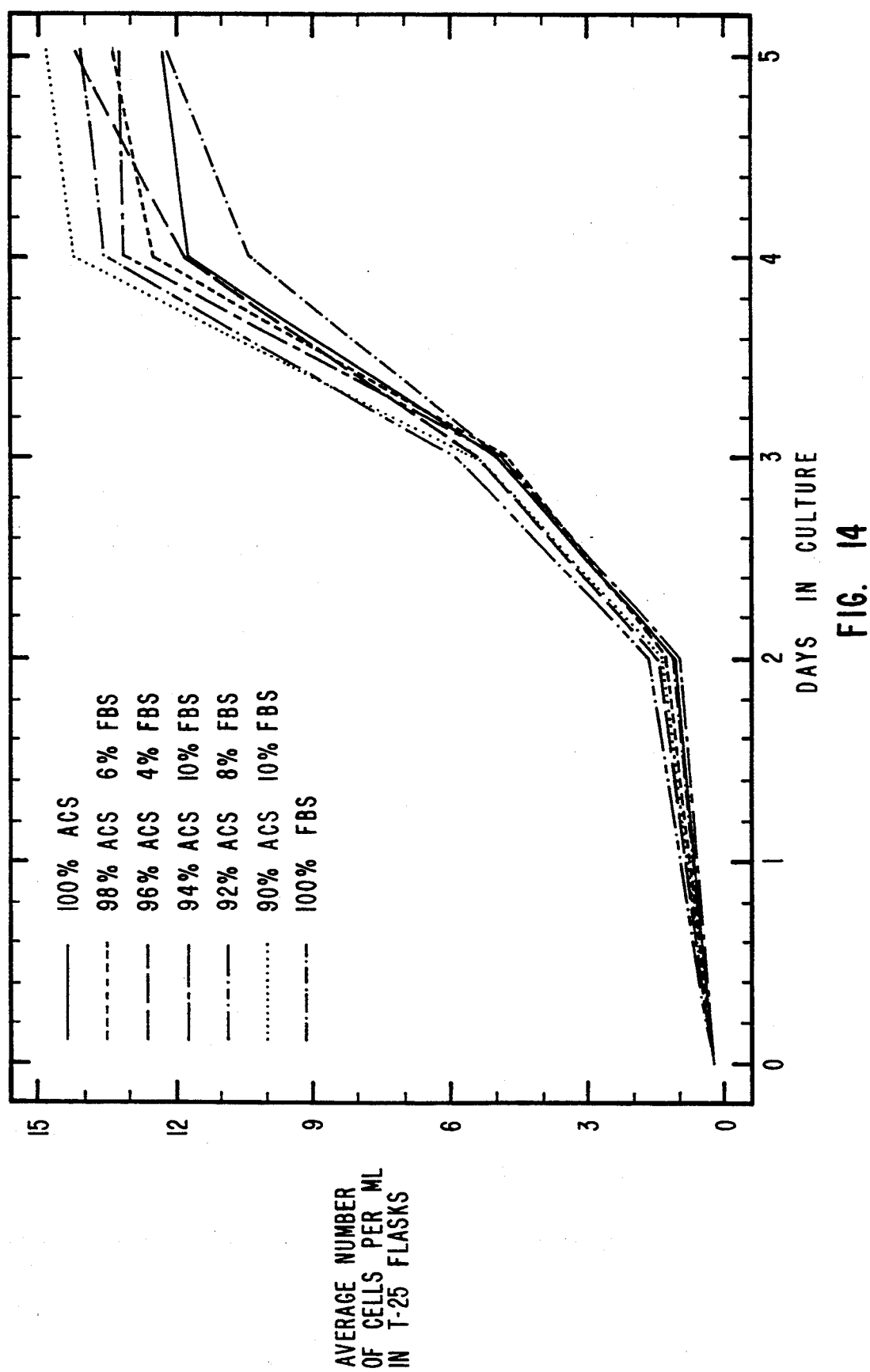
FIG. 14 shows a chart which compares the growth over time of the P3x63-Ag8.653 cellular line in a medium containing various inventive serum blends. The medium has 10% serum in RPMI 1640 medium.

A serum for use in a medium for promoting the growth of a hybridoma cell line was prepared according to example 1, except that the P3x63-Ag8.653 cell line was employed. In addition, the P3x63-Ag8.653 cell line was placed in a media containing RPMI 1640 and a serum blend at a concentration of ten percent (10%). The results of the P3x63-Ag8.653 cell line grown under the foregoing procedures at the various ratios are indicated in FIG. 14.

At 10% serum concentration, blended sera treated cells averaged about $1.48 \times 10^6$ cells/flask, fetal bovine serum treated cells averaged about $1.21 \times 10^6$ cells/flask, and agamma bovine calf serum treated cells averaged $1.22 \times 10^6$ cells/flask. Similar to the Sp2/0 hybrid cell line, the blended sera treated P3x63-Ag8.653 cells exhibited a constant trend of cell growth comparable to fetal bovine serum treated P3x63-Ag8.653 cells.

Example 15

Figure 15:
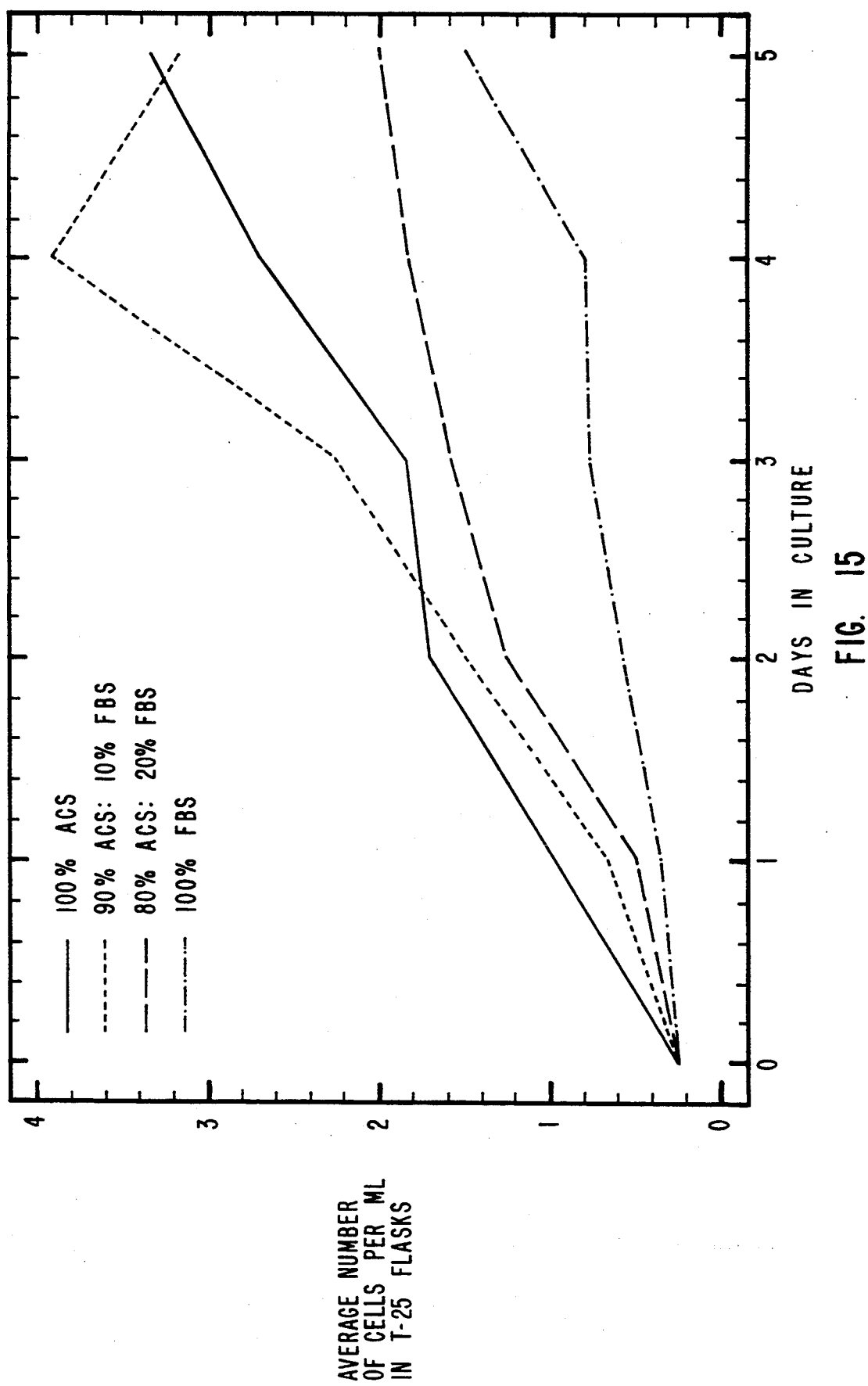
FIG. 15 shows a chart which compares the growth over time of the MOLT-4 cellular line in a medium containing various inventive serum blends. The medium has 10% serum in RPMI 1640 medium.

A serum for use in a medium for promoting the growth of a hybridoma cell line was prepared according to example 1, except that the MOLT-4 cell line was employed. In addition, the MOLT-4 cell line was placed in a media containing RPMI 1640 and a serum blend at a concentration of ten percent (10%). The results of the MOLT-4 cell line grown under the foregoing procedures at the various ratios are indicated in FIG. 15.

The MOLT-4 cells responded in a manner similar to the P3x63-Ag8.653 cell line of Example 14. At 10% serum concentration, blended sera treated cells averaged about $3.18 \times 10^5$ cells/ml, fetal bovine serum treated cells averaged about $1.48 \times 10^5$ cells/ml, and agamma bovine calf serum treated cells averaged $3.34 \times 10^5$ cells/mi. The results illustrate that fetal bovine serum is not always the ideal serum, even though it is usually the serum of choice. The inventive blended serum, in most instances is an equivalent of fetal bovine serum, and in some instances is superior to fetal bovine serum.

Example 16

A cellular culture containing the Sp2/0 hybrid cell line, is grown in the inventive cellular support media by preparing a serum blend to which is added growth factors, hormones, vitamins, sugars, metal salts, nucleotides, amino acids. This type of example is useful to show that the performance of the inventive serum blend to maintain and promote the growth of a cellular line is improved by the addition of growth support factors. By adding purified or partially purified, natural or recombinant technology-derived growth support factors, it is possible to lower the percentage of fetal bovine serum used in the serum blend and therefore, the cost of the serum blend.

Example 17

A cellular culture containing the MRC-5 cellular line is grown in the inventive media by DME medium and 5% serum blend (90% agamma bovine calf serum and 10% Fetal bovine serum) and insulin-like growth factor in a concentration of about 5 ng/ml. This type of example is useful to show that cell growth can be stimulated, and cell yield can be enhanced by the addition of the growth factor. When compared to the cell yields of cellular culture without the growth factor. Also, this example reveals the economic convenience of a lowered serum concentration.

Example 18

A cellular culture containing the SF-9 insect cellular line, is grown in the inventive media by Grace's Insect Tissue Culture medium and 10% serum blend (90% agamma bovine calf serum and 10% fetal bovine serum). This type of example is useful to show that cell growth can be stimulated in this type of cellular line by using the inventive media. This example shows that in this cellular line is grown at 27° C., at ambient $CO_2$ concentration.

Example 19

A cellular culture containing bovine aorta endothelial cells (a primary cell line), is grown in the inventive media by DME medium and 10% serum blend (90% agamma bovine calf serum and 10% fetal bovine serum). This type of example shows that cell growth can be stimulated in this type of cellular line by using the inventive media.

Example 20

A cellular culture containing human epidermal cells (a primary cell line), is grown in the inventive media by DME medium and 10% serum blend (90% agamma bovine calf serum:10% fetal bovine serum). This type of example shows that cell growth can be stimulated in this type of cellular line by using the inventive media.

Example 21

The inventive serum blend (90% agamma bovine calf serum:10% fetal bovine serum) is added in equal proportions to a phosphate buffered saline solution. The mixture is applied to a human stool specimen and placed in a 96 well ELISA plate. Antigen-specific antibodies bound in the ELISA plate selectively bind the antigen in the serum blend/buffer/stool preparation. This type of example illustrates that the inventive serum blend can be used in the construction of diluent or blocking solutions for use in diagnostic kits.

Example 22

A cellular culture containing the Sp2/0 hybrid cell line, is grown in the inventive cellular support media to produce a diagnostic biological. The Sp2/0 hybrid cell line secretes a monoclonal antibody having a distinctive glycosylation pattern. The distinctive glycosylation pattern is identified through experimental testing procedures known to those skilled in the art. This example represents that compositions secreted by organisms maintained or grown in the inventive sera and media have unique characterizations that may be identified and differentiated from similar organisms maintained or grown in noninventive sera and media.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Patent is:

1. A serum blend for use in a medium for maintaining or promoting the growth of cellular lines, wherein the serum blend comprises fetal bovine serum in a concentration in the range from about one percent to about forty percent, agamma bovine calf, serum in a concentration in the range from about sixty percent to about ninety-nine percent, and nutritional components for promoting the growth of cellular lines.

2. The serum blend of claim 1, wherein the agamma bovine calf serum is supplemented with iron prior to blending with the fetal bovine serum.

3. The serum blend of claim 1, wherein the serum blend further comprises an iron supplement.

4. The serum blend of claim 1, wherein the serum blend further comprises an iron supplement in a concentration in the range from about fifty percent to about one hundred percent of the iron-binding capacity of the serum blend.

5. The serum blend of claim 1, wherein the serum blend further comprises an iron supplement in a concentration in the range from about sixty percent to about eighty-five percent of the iron-binding capacity of the serum blend.

6. The serum blend of claim 1, wherein the amount of the fetal bovine serum in the serum blend is in a concentration in the range from about four percent to about twenty percent and agamma bovine calf serum in a concentration in the range from about eighty percent to about ninety-six percent.

7. The serum blend of claim 1, wherein the fetal bovine serum in the serum blend is in a concentration in the range from about six percent to about fifteen percent and agamma bovine calf serum in a concentration in the range from about eighty-five percent to about ninety-four percent.

8. The serum blend of claim 1, wherein the agamma bovine calf serum has a cholesterol concentration in the range from about forty mg/dl to about one hundred twenty mg/dl prior to blending with the fetal bovine serum.

9. The serum blend of claim 1, wherein the agamma bovine calf serum has a triglyceride concentration in the range from about four mg/dl to about ten mg/dl prior to blending with the fetal bovine serum.

10. The serum blend of claim 1, wherein the agamma bovine calf serum has a transferrin level in the range from about four hundred mg/dl to about eight hundred mg/dl prior to blending with the fetal bovine serum.

11. A medium for maintaining or promoting the growth of a cellular line, wherein the medium comprises fetal bovine serum in a concentration in the range from about one percent to about forty percent, agamma bovine calf serum in a concentration in the range from about sixty percent to about ninety-nine percent, nutritional components for promoting the growth of the cellular line, and an iron supplement.

12. The medium of claim 11, wherein the iron supplement is in a concentration in the range from about fifty percent to about one hundred percent of the iron-binding capacity of the serum blend.

13. The medium of claim 11, wherein the iron supplement is in a concentration in the range from about sixty percent to about eighty-five percent of the iron-binding capacity of the serum blend.

14. The medium of claim 11, wherein the fetal bovine serum is in a concentration in the range from about four percent to about twenty percent and agamma bovine calf serum in a concentration in the range from about eighty percent to about ninety-six percent.

15. The medium of claim 11, wherein the fetal bovine serum is in a concentration in the range from about six percent to about fifteen percent and agamma bovine calf serum in a concentration in the range from about eighty-five percent to about ninety-four percent.

16. The medium of claim 11, wherein the agamma bovine calf serum includes a cholesterol concentration in the range from about forty mg/dl to about one hundred twenty mg/dl prior to blending with the fetal bovine serum.

17. The medium of claim 11, wherein the agamma bovine calf serum includes a triglyceride concentration in the range from about four mg/dl to about ten mg/dl prior to blending with the fetal bovine serum.

18. The medium of claim 11, wherein the nutritional components promote the growth of hybridoma cellular lines.

19. The medium of claim 11, wherein the nutritional components promote the growth of attaching cellular lines.

20. A method for preparing a serum blend for use in a medium for maintaining or promoting the growth of cellular lines, wherein the method comprises blending fetal bovine serum in a concentration in the range from about one percent to about forty percent with agamma bovine calf serum in a concentration in the range from about sixty percent to about ninety-nine percent.

21. The method of claim 20, wherein the agamma bovine calf serum is supplemented with iron prior to blending with the fetal bovine serum.

22. The method of claim 20, wherein the agamma bovine calf serum includes a lipid concentration in the range from about five mg/dl to about one hundred twenty mg/dl prior to blending with the fetal bovine serum.

23. The method of claim 20, wherein the agamma bovine calf serum has a transferrin level in the range from about four hundred mg/dl to about eight hundred mg/dl prior to blending with the fetal bovine serum.

24. The method of claim 20, wherein said blending comprises adding fetal bovine serum in a concentration in the range from about four percent to about twenty percent to the agamma bovine calf serum in a concentration in the range from about eighty percent to about ninety-six percent.

25. The method of claim 20, wherein said blending comprises adding the fetal bovine serum in a concentration in the range from about six percent to about fifteen percent to the agamma bovine, calf serum in a concentration in the range from about eighty-five percent to about ninety-four percent.

26. The method of claim 20, wherein the method further comprises adding an iron supplement to the medium.

27. The method of claim 26, wherein a solution containing an iron supplement is added to the medium.

28. The method of claim 26, wherein the iron supplement is added to the medium in a concentration in the range from about fifty percent to about one hundred percent of the iron-binding capacity of the medium.

29. The method of claim 26, wherein the iron supplement is added to the medium in a concentration in the range from about sixty percent to about eighty-five percent of the iron-binding capacity of the medium.

30. The method of claim 26, wherein the method further comprises sterilizing the medium.

31. The method of claim 30, wherein the medium is sterilized by filtering the medium.

32. The method of claim 20, wherein the method further comprises adding a basal culture medium to the serum blend.

33. The method of claim 32, wherein said basal culture medium is Dulbecco's Modified Eagle's Medium.

34. The method of claim 20, wherein the agamma bovine calf serum has a cholesterol concentration in the range from about forty mg/dl to about one hundred twenty mg/dl prior to blending with the fetal bovine serum.

35. The method of claim 20, wherein the agamma bovine calf serum has a triglyceride concentration in the range from about four mg/dl to about ten mg/dl prior to blending with the fetal bovine serum.

36. A method for preparing a medium for maintaining or promoting the growth of a cellular line, wherein the method comprises:
blending fetal bovine serum in a concentration in the range from about one percent to about forty percent with agamma bovine calf serum in a concentration in the range from about sixty percent to about ninety-nine percent to form a serum blend; and
adding to the serum blend a basal culture medium.

37. The method of claim 36, wherein the agamma bovine calf serum includes iron supplementation prior to blending with the fetal bovine serum.

38. The method of claim 36, wherein said blending comprises adding fetal bovine serum in a concentration in the range from about four percent to about twenty percent and agamma bovine calf serum in a concentration in the range from about eighty percent to about ninety-six percent.

39. The method of claim 36, wherein said blending comprises adding fetal bovine serum in a concentration in the range from about six percent to about fifteen percent and agamma bovine calf serum in a concentration in the range from about eighty-five percent to about ninety-four percent.

40. The method of claim 36, wherein the method further comprises adding an iron supplement to the medium.

41. The method of claim 40, wherein the iron supplement is added to the medium in the concentration in the range from about fifty percent to about one hundred percent of the total binding capacity of the medium.

42. The method of claim 40, wherein the iron supplement is added to the medium in the concentration in the range from about sixty percent to about eighty-five percent of the iron-binding capacity of the medium.

43. The method of claim 36, wherein the method farther comprises sterilizing the medium.

44. The method of claim 36, wherein said basal culture medium, is Dulbecco's Modified Eagle's Medium.

45. The method of claim 36, wherein the agamma bovine calf serum has a cholesterol concentration in the range from about forty to about one hundred twenty mg/dl prior to blending with the fetal bovine serum.

46. The method of claim 36, wherein the agamma bovine calf serum has a triglyceride concentration in the range from about four to about ten mg/dl prior to blending with the fetal bovine serum.

47. The method of claim 36, wherein the method farther comprises adding nutritional components to the medium, said nutritional components are capable of maintaining or promoting the growth of cellular lines.

48. The method of claim 36, wherein the method further comprises adding nutritional components to the medium, said nutritional components are capable of maintaining or promoting the growth of attaching cellular lines.

49. A method for growing cells, wherein the method comprises:
obtaining a cellular line; and
culturing said cellular line in a medium that maintains and promotes the growth of said cellular line, said medium comprises fetal bovine serum in a concentration in the range from about one percent to about forty percent and agamma bovine calf serum in a concentration in the range from about sixty percent to about ninety-nine percent, said agamma bovine calf serum has a lipid concentration in the range from about five mg/dl to about one hundred and twenty mg/dl.

50. The method of claim 49, wherein said fetal bovine serum is in a concentration in the range from about four percent to about twenty percent and said agamma bovine calf serum is in a concentration in the range from about eighty percent to about ninety-six percent.

51. The method of claim 49, wherein said fetal bovine serum is in a concentration in the range from about six percent to about fifteen percent and said agamma bovine calf serum is in a concentration in the range from about eighty-five percent to about ninety-four percent.

52. The method of claim 49, wherein said medium further comprises agarose.

53. The method of claim 49, wherein said medium further comprises a basal culture medium.

54. The method of claim 53, wherein said basal culture medium is Dulbecco's Modified Eagle's Medium.

55. The method of claim 49, wherein the cellular line is a hybridoma cellular line.

56. The method of claim 49, wherein the cellular line is an attaching cellular line.

57. The method of claim 49, wherein the cellular line is a non-attaching cellular line.

58. The method of claim 55, wherein the hybridoma cellular line is a Sp2/0 cellular line.

59. The method of claim 57, wherein the non-attaching cellular line is a P3X63-Ag8.653 cellular line.

60. The method of claim 49, wherein said culturing occurs in a $CO_2$ atmosphere in the range from about ambient level to about ten percent $CO_2$-enriched atmosphere.

61. The method of claim 60, wherein said culturing occurs at a temperature in the range from about 25° C. to about 42° C..

62. The method of claim 60, wherein said culturing occurs at a temperature in the range from about 35° C. to about 40° C2.

63. The method of claim 49, wherein the agamma bovine calf serum has a cholesterol concentration in the range from about forty mg/dl to about one hundred twenty mg/dl.

64. The method of claim 49, wherein the agamma bovine calf serum has a triglyceride concentration in the range from about four mg/dl to about ten mg/dl.

* * * * *

UNITED STATES PATENT AND TRADEMARK OFFICE
CERTIFICATE OF CORRECTION

PATENT NO. : 5,409,827  Page 1 of 2
DATED : April 25, 1995
INVENTOR(S) : Dale G. Kern It is certified that error appears in the above-indentified patent and that said Letters Patent is hereby corrected as shown below:

Column 1, line 18, delete ":".

Column 2, line 33, "i.e ,," should be --i.e.,--.

Column 3, line 15, " can not" should be --cannot--.

Column 4, line 32, "ally" should be --any--.

Column 5, line 2, after "(85%)" insert --to--.

Column 8, line 36, "some of some of" should be --some of--.

Column 9, line 68, delete ";".

Column 13, line 20, "is" should be --are--.

Column 14, line 33, after "studies" insert --by--.

Column 14, lines 59-60, "antibody" should be --antibodies--.

Column 14, line 66, "J. Kearney et ill." should be --J. Kearney et al.--.

Column 15, line 30, after "from" insert --the--.

Column 15, line 33, "electroll" should be --electron--.

Column 15, line 42, after "relapse" insert --.--.

Column 15, line 42, "it" should be --It--.

Column 16, line 16, "invention blended sera was" should be --invention, blended sera, was--.

Column 16, line 33, "filter-sterilize&" should be --filter-sterilized--.

UNITED STATES PATENT AND TRADEMARK OFFICE
CERTIFICATE OF CORRECTION

PATENT NO.  : 5,409,827
DATED       : April 25, 1995
INVENTOR(S) : Dale G. Kern

It is certified that error appears in the above-indentified patent and that said Letters Patent is hereby corrected as shown below:

Column 16, lines 67-68, "sapabilities" should be --capabilities--.
Column 20, line 18, "the day 7," should be --day 7,--.
Column 20, line 47, "Sp2/Ohybrid" should be --Sp2/O hybrid--.
Column 20, line 48, "Cells" should be --cells--.
Column 22, line 17, "growth factor. When compared" should be --growth factor when compared--.
Column 24, line 68, delete ",".
Column 26, line 4, "farther" should be --further--.
Column 27, line 6, "(2." should be deleted and replaced with -- C.--.

Signed and Sealed this

Thirty-first Day of October 1995

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,409,827
DATED : April 25, 1995
INVENTOR(S) : Dale G. Kern

It is certified that error appears in the above-identified patent and that said Letters Patent is hereby corrected as shown below:

Column 23,
Line 22, after "bovine" change "call," to -- calf --
Line 50, before "agamma" insert -- the --
Line 50, after "serum" insert -- is --

Column 24,
Line 16, before "agamma" insert -- the --
Line 17, after "serum" insert -- is --
Line 21, before "agamma" insert -- the --
Line 22, after "serum" insert -- is --
Line 25, change ":serum" to -- serum --

Signed and Sealed this

Twenty-ninth Day of June, 2004

JON W. DUDAS
*Acting Director of the United States Patent and Trademark Office*